United States Patent
Vo et al.

(10) Patent No.: US 9,843,001 B2
(45) Date of Patent: Dec. 12, 2017

(54) BLUE LUMINESCENT COMPOUNDS

(71) Applicant: E I DU PONT DE NEMOURS AND COMPANY, Wilmington, DE (US)

(72) Inventors: Giang Dong Vo, Wilmington, DE (US); Troy C Gehret, Wilmington, DE (US); Kyung-Ho Park, Wilmington, DE (US); Ying Wang, West Chester, PA (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 701 days.

(21) Appl. No.: 14/462,053

(22) Filed: Aug. 18, 2014

(65) Prior Publication Data

US 2016/0049598 A1    Feb. 18, 2016

(51) Int. Cl.
| | | |
|---|---|---|
| H01L 51/54 | (2006.01) | |
| C09K 11/06 | (2006.01) | |
| C07D 403/04 | (2006.01) | |
| H01L 51/00 | (2006.01) | |
| C07F 15/00 | (2006.01) | |
| H01L 51/50 | (2006.01) | |

(52) U.S. Cl.
CPC ........ H01L 51/0085 (2013.01); C07D 403/04 (2013.01); C07F 15/0033 (2013.01); C09K 11/06 (2013.01); C09K 2211/1044 (2013.01); C09K 2211/1059 (2013.01); C09K 2211/185 (2013.01); H01L 51/0072 (2013.01); H01L 51/0073 (2013.01); H01L 51/5016 (2013.01)

(58) Field of Classification Search
None
See application file for complete search history.

(56) References Cited

U.S. PATENT DOCUMENTS

| | | | |
|---|---|---|---|
| 6,670,645 B2 | 12/2003 | Grushin et al. | |
| 6,875,524 B2 | 4/2005 | Hatwar et al. | |
| 2002/0076576 A1* | 6/2002 | Li et al. | H01L 51/0038 428/690 |
| 2004/0102577 A1 | 5/2004 | Hsu et al. | |
| 2004/0127637 A1 | 7/2004 | Hsu et al. | |
| 2005/0158577 A1 | 7/2005 | Ishibashi et al. | |
| 2005/0205860 A1 | 9/2005 | Hsu et al. | |
| 2009/0102370 A1* | 4/2009 | Taka et al. | C07D 233/58 313/504 |
| 2012/0025178 A1* | 2/2012 | Inoue et al. | C07F 15/0033 257/40 |

FOREIGN PATENT DOCUMENTS

| | | |
|---|---|---|
| WO | 03/008424 A1 | 1/2003 |
| WO | 03/040257 A1 | 5/2003 |
| WO | 03/091688 A2 | 11/2003 |
| WO | 2004/016710 A1 | 2/2004 |
| WO | 2004/101707 A1 | 11/2004 |
| WO | 2009/018009 A1 | 2/2009 |
| WO | 2009/067419 A1 | 5/2009 |
| WO | 2011/064335 A1 | 6/2011 |

OTHER PUBLICATIONS

Gustafsson et al, "Flexible Light-Emitting Diodoes Made From Soluble Conducting Polymers", Nature, vol. 357, pp. 477-479, Jun. 11, 1992.

\* cited by examiner

*Primary Examiner* — Marie R. Yamnitzky

(57) ABSTRACT

There is provided a compound having Formula II

[Structure of Formula II showing an iridium complex with R$^1$, R$^2$, R$^3$, R$^4$ substituents and (R$^2$)$_a$ group]

In Formula II: R$^1$ and R$^3$ are the same of different and can be alkyl, branched alkyl, cyclic alkyl, silyl, aryl, deuterated alkyl, deuterated branched alkyl, deuterated cyclic alkyl, deuterated silyl, and deuterated aryl; R$^2$ is the same or different at each occurrence and can be D, alkyl, branched alkyl, cyclic alkyl, silyl, aryl, deuterated alkyl, deuterated branched alkyl, deuterated cyclic alkyl, deuterated silyl, and deuterated aryl; R$^4$ can be H or D; and a is an integer from 0-5.

18 Claims, 2 Drawing Sheets

BLUE LUMINESCENT COMPOUNDS

BACKGROUND INFORMATION

Field of the Disclosure

This disclosure relates in general to blue luminescent compounds and their use in electronic devices.

Description of the Related Art

Organic electronic devices that emit light, such as light-emitting diodes that make up displays, are present in many different kinds of electronic equipment. In all such devices, an organic active layer is sandwiched between two electrical contact layers. At least one of the electrical contact layers is light-transmitting so that light can pass through the electrical contact layer. The organic active layer emits light through the light-transmitting electrical contact layer upon application of electricity across the electrical contact layers.

It is well known to use organic electroluminescent compounds as the active component in light-emitting diodes. Simple organic molecules, such as anthracene, thiadiazole derivatives, and coumarin derivatives are known to show electroluminescence. Metal complexes, particularly iridium and platinum complexes are also known to show electroluminescence. In some cases these small molecule compounds are present as a dopant in a host material to improve processing and/or electronic properties.

There is a continuing need for new luminescent compounds.

SUMMARY

There is provided a compound having Formula I

Formula I wherein:
  $R^1$ and $R^3$ are the same or different and are selected from the group consisting of alkyl, branched alkyl, cyclic alkyl, silyl, aryl, deuterated alkyl, deuterated branched alkyl, deuterated cyclic alkyl, deuterated silyl, and deuterated aryl;
  $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
  $R^4$-$R^5$ are the same or different at each occurrence and are H or D; and
  a is an integer from 0-5.

There is also provided a material having Formula II

Formula II wherein:
  $R^1$ and $R^3$ are the same or different and are selected from the group consisting of alkyl, branched alkyl, cyclic alkyl, silyl, aryl, deuterated alkyl, deuterated branched alkyl, deuterated silyl, and deuterated aryl;
  $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
  $R^4$ is H or D; and
  a is an integer from 0-5.

There is also provided an organic electronic device comprising a first electrical contact, a second electrical contact and a photoactive layer there between, the photoactive layer comprising the material having Formula II.

The foregoing general description and the following detailed description are exemplary and explanatory only and are not restrictive of the invention, as defined in the appended claims.

BRIEF DESCRIPTION OF THE DRAWINGS

Embodiments are illustrated in the accompanying figures to improve understanding of concepts as presented herein.

Figure 1:
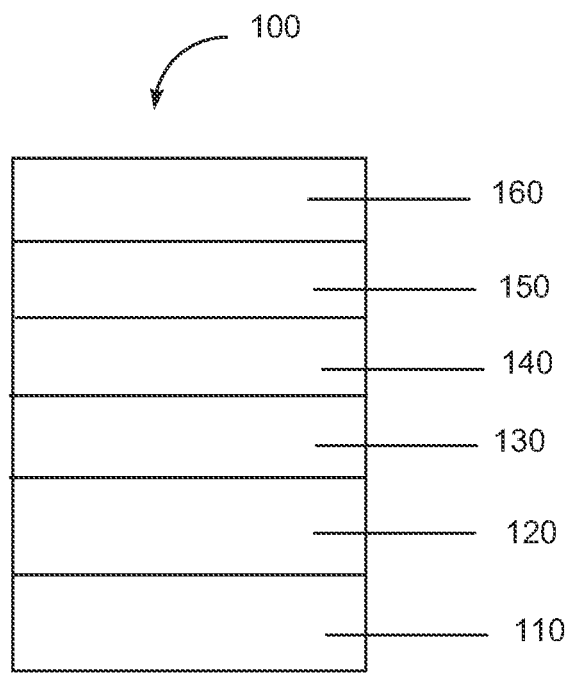
FIG. 1 includes an illustration of an organic light-emitting device.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

Many aspects and embodiments have been described above and are merely exemplary and not limiting. After reading this specification, skilled artisans appreciate that other aspects and embodiments are possible without departing from the scope of the invention.

Other features and benefits of any one or more of the embodiments will be apparent from the following detailed description and from the claims. The detailed description first addresses Definitions and Clarification of Terms followed by the Material Having Formula I or Formula II, Synthesis, Devices, and finally Examples.

1. Definitions and Clarification of Terms

Before addressing details of embodiments described below, some terms are defined or clarified.

The term "alkyl" is intended to mean a group derived from an aliphatic hydrocarbon and includes a linear, a branched, or a cyclic group. In some embodiments, an alkyl has from 1-20 carbon atoms.

The term "anti-quenching" when referring to a layer or material, refers to such layer or material which prevents quenching of blue luminance by the electron transport layer, either via an energy transfer or an electron transfer process.

The term "aromatic compound" is intended to mean an organic compound comprising at least one unsaturated cyclic group having delocalized pi electrons. The aromatic ring has 4n+2 pi electrons and is essentially planar.

The term "aryl" is intended to mean a group derived from an aromatic hydrocarbon having one point of attachment. The term includes groups which have a single ring and those which have multiple rings which can be joined by a single bond or fused together. The term is intended to include both hydrocarbon aryls, having only carbon in the ring structure, and heteroaryls. The term "alkylaryl" is intended to mean an aryl group having one or more alkyl substituents. In some embodiments, a hydrocarbon aryl has 6-60 ring carbons. In some embodiments, a heteroaryl has 3-60 ring carbons.

The term "branched alkyl" is intended to mean a group derived from an aliphatic hydrocarbon that has at least one secondary or tertiary carbon. A secondary alkyl group has the structure:

where the R groups are the same or different and are alkyl groups and the asterisk represents the point of attachment to the triazole ring. An exemplary secondary alkyl group is an isopropyl group. A tertiary alkyl group has the structure:

where the R groups are the same or different and are alkyl groups and the asterisk represents the point of attachment to the triazole ring. An exemplary tertiary alkyl group is a t-butyl group.

The term "charge transport," when referring to a layer, material, member, or structure is intended to mean such layer, material, member, or structure facilitates migration of such charge through the thickness of such layer, material, member, or structure with relative efficiency and small loss of charge. Hole transport materials facilitate positive charge; electron transport materials facilitate negative charge. Although light-emitting materials may also have some charge transport properties, the term "charge transport layer, material, member, or structure" is not intended to include a layer, material, member, or structure whose primary function is light emission.

The term "cyclic alkyl" is intended to mean a group derived from an aliphatic hydrocarbon that has 4-20 carbon atoms in an aliphatic ring. The ring may have on or more double bonds but is not aromatic. A cyclic alkyl may be monocyclic or polycyclic.

The term "deuterated" is intended to mean that at least one hydrogen has been replaced by deuterium, abbreviated herein as "D". The term "deuterated analog" refers to a structural analog of a compound or group in which one or more available hydrogens have been replaced with deuterium. In a deuterated compound or deuterated analog, the deuterium is present in at least 100 times the natural abundance level.

The term "dopant" is intended to mean a material, within a layer including a host material, that changes the electronic characteristic(s) or the targeted wavelength(s) of radiation emission, reception, or filtering of the layer compared to the electronic characteristic(s) or the wavelength(s) of radiation emission, reception, or filtering of the layer in the absence of such material.

The prefix "hetero" indicates that one or more carbon atoms have been replaced with a different atom. In some embodiments, the different atom is N, O, or S.

The term "host material" is intended to mean a material, usually in the form of a layer, to which a dopant may be added. The host material may or may not have electronic characteristic(s) or the ability to emit, receive, or filter radiation.

The terms "luminescent material" and "emitter" are intended to mean a material that emits light when activated by an applied voltage (such as in a light-emitting diode or light-emitting electrochemical cell).

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating or printing. Discontinuous deposition techniques include, but are not limited to, ink jet printing, gravure printing, and screen printing.

The term "organic electronic device" or sometimes just "electronic device" is intended to mean a device including one or more organic semiconductor layers or materials.

The term "photoactive" refers to a material or layer that emits light when activated by an applied voltage (such as in a light emitting diode or chemical cell) or responds to radiant energy and generates a signal with or without an applied bias voltage (such as in a photodetector or a photovoltaic cell).

All groups may be unsubstituted or substituted. The substituent groups are discussed below.

In this specification, unless explicitly stated otherwise or indicated to the contrary by the context of usage, where an embodiment of the subject matter hereof is stated or described as comprising, including, containing, having, being composed of or being constituted by or of certain features or elements, one or more features or elements in addition to those explicitly stated or described may be present in the embodiment. An alternative embodiment of the disclosed subject matter hereof, is described as consisting essentially of certain features or elements, in which embodiment features or elements that would materially alter the principle of operation or the distinguishing characteristics of the embodiment are not present therein. A further alternative embodiment of the described subject matter hereof is described as consisting of certain features or elements, in which embodiment, or in insubstantial variations thereof, only the features or elements specifically stated or described are present.

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. In case of conflict, the present specification, including definitions, will control. In addition, the materials, methods, and examples are illustrative only and not intended to be limiting.

To the extent not described herein, many details regarding specific materials, processing acts, and circuits are conventional and may be found in textbooks and other sources within the organic light-emitting diode display, photodetector, photovoltaic cell, and semiconductive member arts.

2. Compounds Having Formula I or Formula II

There is provided herein a new compound having Formula I

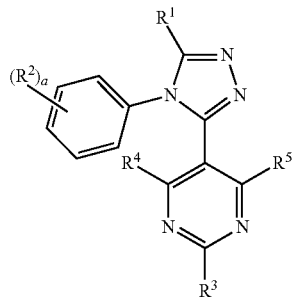

Formula I wherein:
  $R^1$ and $R^3$ are the same or different and are selected from the group consisting of alkyl, branched alkyl, cyclic alkyl, silyl, aryl, deuterated alkyl, deuterated branched alkyl, deuterated cyclic alkyl, deuterated silyl, and deuterated aryl;
  $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
  $R^4$-$R^5$ are the same or different at each occurrence and are H or D; and
  a is an integer from 0-5.

The new compounds having Formula I can be used as ligands to form transition metal complexes.

In some embodiments, the transition metal complexes include the compounds of Formula I coordinated to metals selected from the group including Pt, Os, Ru, Rh, and Ir.

The new compounds having Formula I can be used as ligands to form metal complexes having Formula II

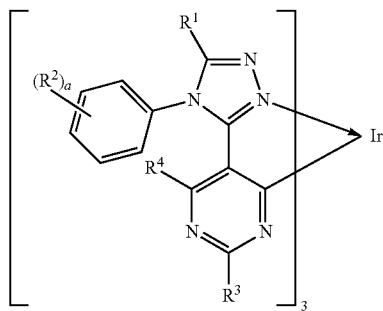

Formula II wherein:
  $R^1$ and $R^3$ are the same or different and are selected from the group consisting of alkyl, branched alkyl, cyclic alkyl, silyl, aryl, deuterated alkyl, deuterated branched alkyl, deuterated cyclic alkyl, deuterated silyl, and deuterated aryl;
  $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
  $R^4$ is H or D; and
  a is an integer from 0-5.

In some embodiments, the compounds having Formula II are useful as emissive materials. The compound having Formula II are capable of blue electroluminescence. The compounds can be used alone or as a dopant in a host material.

The compounds having Formula II are soluble in many commonly used organic solvents. Solutions of these compounds can be used for liquid deposition using techniques such as discussed above. Surprisingly, it has been found that compounds containing greater than one nitrogen atom in the six-membered ring coordinated to the metal center, such as pyrimidine, produce a shift in emission towards blue versus analogous compounds that do not contain more than one nitrogen atom in the six-membered ring.

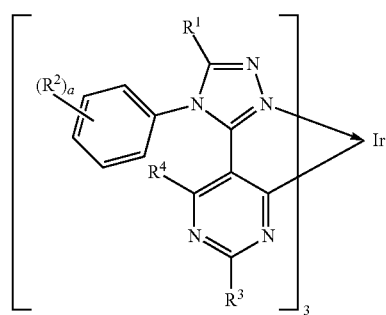

The shift toward blue can be seen as a decrease in the wavelength of the peak of maximum emission. The shift toward blue can be seen as a decrease in the color coordinates of emission, according to the chromaticity scale.

In some embodiments, the compounds have an electroluminescent ("EL") peak less than 500 nm. In some embodiments, the compounds have an EL peak in the range of 445-490 nm. In some embodiments, the compounds have an EL peak in the range 440-460 nm. In some embodiments, the compounds used in devices result in color coordinates of x<0.25 and y<0.5, according to the 1931 C.I.E. convention (Commission Internationale de L'Eclairage, 1931). In some embodiments, the color coordinates are x<0.30 and y<0.40; in some embodiments, x<0.18 and y<0.15.

Also such compounds may provide other advantages in electronic devices. In some embodiments with certain architectures, devices made with compounds having Formula II may have improved efficiencies and lifetimes. This is advantageous for reducing energy consumption in all types of devices, and particularly for lighting applications. Higher efficiency also improves device lifetime at constant luminance.

Specific embodiments of the present invention include, but are not limited to, the following.

In some embodiments, the compound of Formula I or Formula II is deuterated.

In some embodiments, the compound of Formula I or Formula II is at least 10% deuterated. By "% deuterated" or "% deuteration" is meant the ratio of deuterons to the total of hydrogens plus deuterons, expressed as a percentage. The deuteriums may be on the same or different groups.

In some embodiments, the compound of Formula I or Formula II is at least 25% deuterated.

In some embodiments, the compound of Formula I or Formula II is at least 50% deuterated.

In some embodiments, the compound of Formula I or Formula II is at least 75% deuterated.

In some embodiments, the compound of Formula I or Formula II is at least 90% deuterated.

In some embodiments of the compound of Formula I or Formula II, $R^1$ and $R^3$ are an alkyl or deuterated alkyl group having 3-20 carbons.

In some embodiments of the compound of Formula I or Formula II, $R^1$ and $R^3$ are an alkyl or deuterated alkyl group having 3-12 carbons.

In some embodiments of the compound of Formula I or Formula II, $R^1$ and $R^3$ are an alkyl or deuterated alkyl group having 3-6 carbons.

In some embodiments of the compound of Formula I or Formula II, $R^1$ and $R^3$ are a branched alkyl or deuterated branched alkyl group having 3-20 carbons.

In some embodiments of the compound of Formula I or Formula II, $R^1$ and $R^3$ are a branched alkyl or deuterated branched alkyl group having 3-10 carbons, and the branch occurs at a secondary or tertiary carbon atom that is directly bound to the triazole ring. Further branching may occur at other locations on $R^1$ and $R^3$.

In some embodiments of the compound of Formula I or Formula II, $R^1$ and $R^3$ are a branched alkyl or deuterated branched alkyl group having 4-6 carbons.

In some embodiments of the compound of Formula I or Formula II, $R^1$ and $R^3$ are a monocyclic alkyl or deuterated monocyclic alkyl group having 4-20 ring carbons. Multiple cycloalkyl groups may be present.

In some embodiments of the compound of Formula I or Formula II, $R^1$ and $R^3$ are a monocyclic alkyl or deuterated monocyclic alkyl group having 6-12 ring carbons.

In some embodiments of the compound of Formula I or Formula II, $R^1$ and $R^3$ are a monocyclic alkyl or deuterated monocyclic alkyl group having 8-10 ring carbons.

In some embodiments of the compound of Formula I or Formula II, $R^1$ and $R^3$ are a polycyclic alkyl or deuterated polycyclic alkyl group having 6-20 ring carbons.

In some embodiments of the compound of Formula I or Formula II, $R^1$ and $R^3$ are a polycyclic alkyl or deuterated polycyclic alkyl group having 8-12 ring carbons.

In some embodiments of the compound of Formula I or Formula II, $R^1$ and $R^3$ are a silyl or deuterated silyl group having 3-6 carbons.

In some embodiments of the compound of Formula I or Formula II, $R^1$ and $R^3$ are an aryl or deuterated aryl group having 6-12 carbons. The aryl or deuterated aryl groups may be further substituted at any available positions. In some embodiments, the further substituent groups are selected from alkyl, branched alkyl, aryl, and deuterated analogs thereof.

In some embodiments of the compound of Formula I or Formula II, $R^1$ and $R^3$ are the same group.

In some embodiments of the compound of Formula I or Formula II, $R^1$ and $R^3$ are different groups.

In some embodiments of the compound of Formula I or Formula II, a=0.

In some embodiments of the compound of Formula I or Formula II, a=1.

In some embodiments of the compound of Formula I or Formula II, a=2.

In some embodiments of the compound of Formula I or Formula II, a=3.

In some embodiments of the compound of Formula I or Formula II, a=4.

In some embodiments of the compound of Formula I or Formula II, a=5.

In some embodiments of the compound of Formula I or Formula II, a>0 and $R^2$ is D.

In some embodiments of the compound of Formula I or Formula II, a>0 and $R^2$ is an alkyl or deuterated alkyl group having 1-6 carbons.

In some embodiments of the compound of Formula I or Formula II, a>0 and $R^2$ is a branched alkyl or deuterated branched alkyl group having 3-20 carbons.

In some embodiments of the compound of Formula I or Formula II, a>0 and $R^2$ is a branched alkyl or deuterated branched alkyl group having 3-10 carbons, and the branch occurs at a secondary or tertiary carbon atom that is directly bound to the aromatic ring. Further branching may occur at other locations on $R^2$.

In some embodiments of the compound of Formula I or Formula II, a>0 and $R^2$ is a branched alkyl or deuterated branched alkyl group having 4-6 carbons.

In some embodiments of the compound of Formula I or Formula II, a>0 and $R^2$ is a cyclic alkyl or deuterated cyclic alkyl group having 4-20 ring carbons.

In some embodiments of the compound of Formula I or Formula II, a>0 and $R^2$ is a silyl or deuterated silyl group having 3-6 carbons.

In some embodiments of the compound of Formula I or Formula II, a>0 and $R^2$ is an aryl or deuterated aryl group having 6-12 carbons. The aryl or deuterated aryl groups may be further substituted at any available positions.

Any of the above embodiments can be combined with one or more of the other embodiments, so long as they are not mutually exclusive. For example, the embodiment in which $R^1$ and $R^3$ are branched alkyl or deuterated branched alkyl groups having 4-6 carbons can be combined with the embodiment in which a>0 and $R^2$ is an alkyl or deuterated alkyl group having 1-6 carbons. The same is true for the other non-mutually-exclusive embodiments discussed above. The skilled person would understand which embodiments were mutually exclusive and would thus readily be able to determine the combinations of embodiments that are contemplated by the present application.

Examples of compounds having Formula I include, but are not limited to, the compounds shown below.

Compound L1

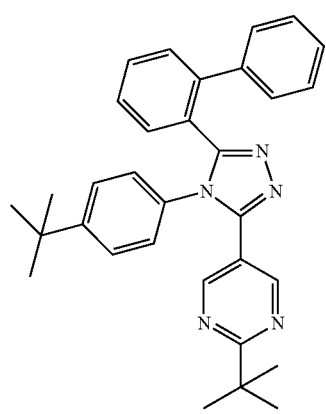

Compound L2

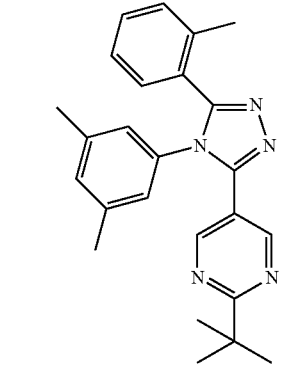

Compound L3

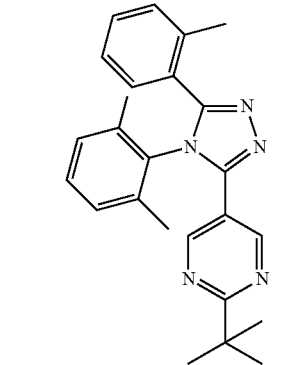

Compound L4

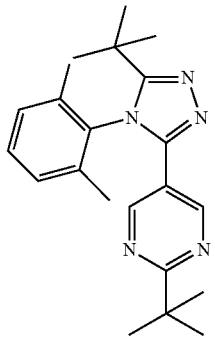

Compound L5

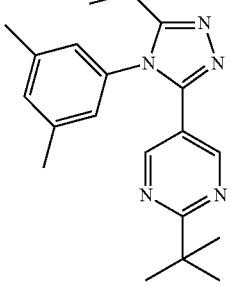

Compound L6

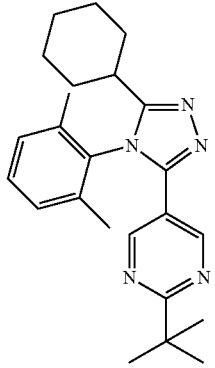

Examples of compounds having Formula II include, but are not limited to, the compounds shown below.

Compound B1

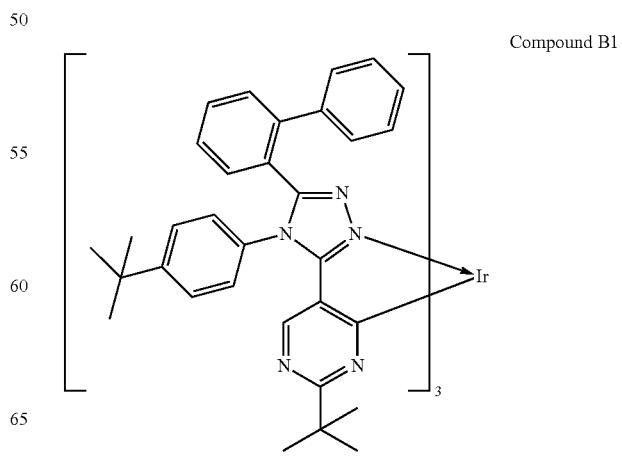

Compound B2
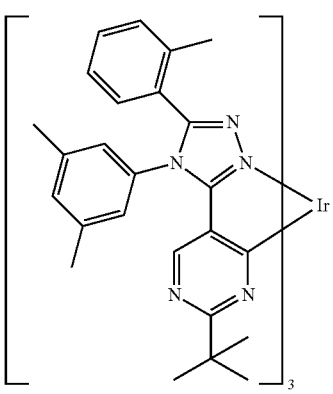
Compound B3
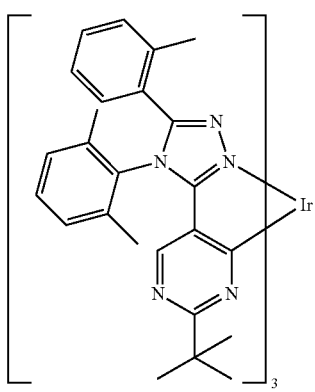
Compoound B4
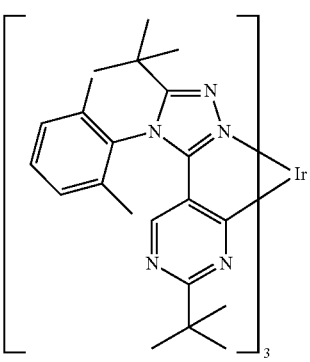
Compound B5
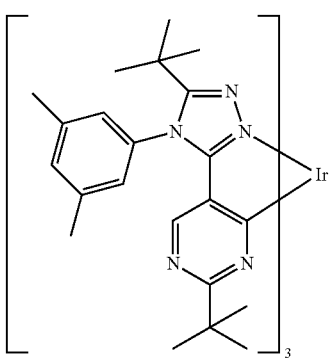
Compound B6
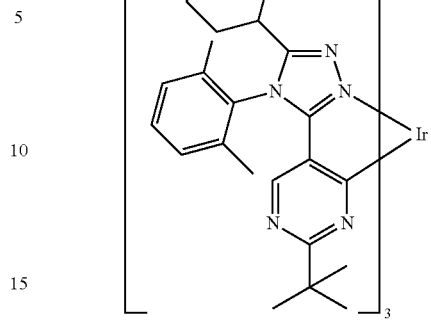
3. Synthesis
The compounds having Formula I described herein can be synthesized by a variety of procedures that have precedent in the literature. The exact procedure chosen will depend on a variety of factors, including availability of starting materials and reaction yield.
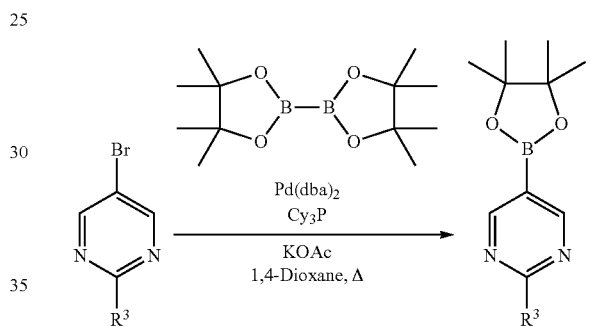
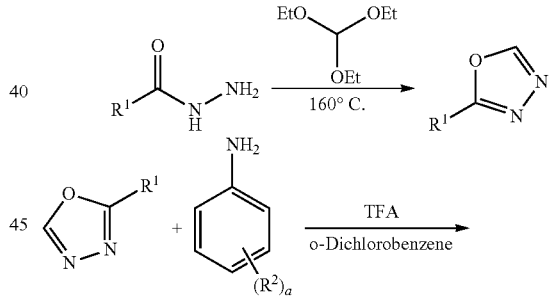
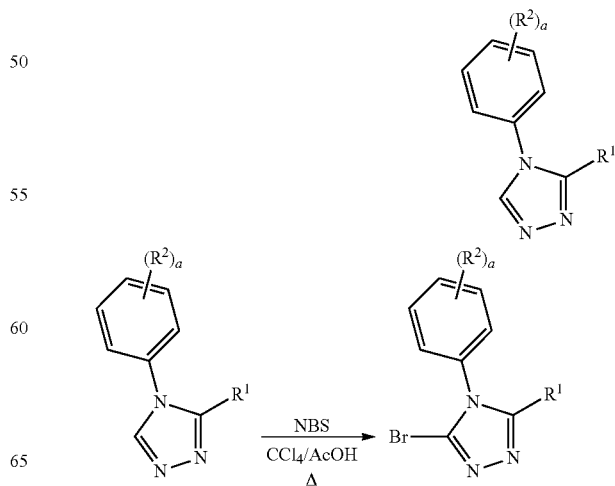

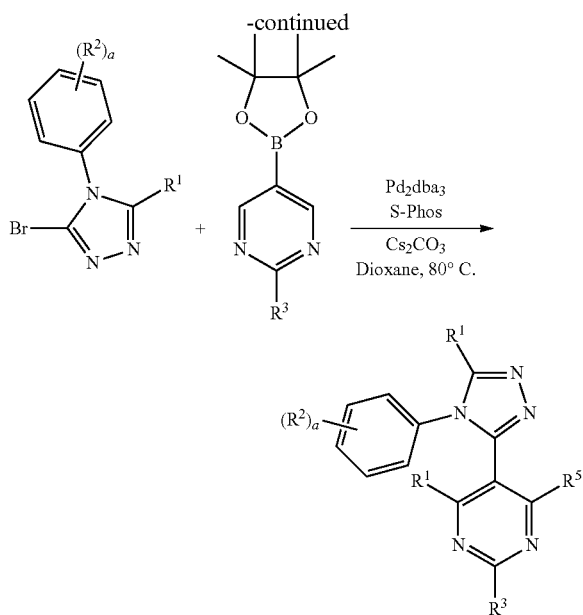

The compounds having Formula II can be prepared by the reaction of commercially available Ir(acetylacetonate)₃ with excess ligand at elevated temperatures. This reaction typically results in cyclometallation of three equivalents of ligand onto iridium and formation of three equivalents of acetylacetone. The IrL₃ product, wherein L is the cyclometallated ligand, can be isolated and purified by chromatography and/or recrystallization.

4. Devices

Organic electronic devices that may benefit from having one or more layers comprising the compounds having Formula II described herein include, but are not limited to: (1) devices that convert electrical energy into radiation (e.g., a light-emitting diode, light emitting diode display, diode laser, or lighting panel), (2) devices that detect a signal using an electronic process (e.g., a photodetector, a photoconductive cell, a photoresistor, a photoswitch, a phototransistor, a phototube, an infrared ("IR") detector, or a biosensors), (3) devices that convert radiation into electrical energy (e.g., a photovoltaic device or solar cell), (4) devices that convert light of one wavelength to light of a longer wavelength, (e.g., a down-converting phosphor device); (5) devices that include one or more electronic components that include one or more organic semiconductor layers (e.g., a transistor or diode), or any combination of devices in items (1) through (5).

One illustration of an organic electronic device structure is shown in FIG. 1. The device 100 has a first electrical contact layer, an anode layer 110 and a second electrical contact layer, a cathode layer 160, and a photoactive layer 140 between them. Adjacent to the anode is a hole injection layer 120. Adjacent to the hole injection layer is a hole transport layer 130, comprising hole transport material. Adjacent to the cathode may be an electron transport layer 150, comprising an electron transport material. As an option, devices may use one or more additional hole injection or hole transport layers (not shown) next to the anode 110 and/or one or more additional electron injection or electron transport layers (not shown) next to the cathode 160. As a further option, devices may have an anti-quenching layer (not shown) between the photoactive layer 140 and the electron transport layer 150.

Layers 120 through 150, and any additional layers between them, are individually and collectively referred to as the active layers.

Figure 2:
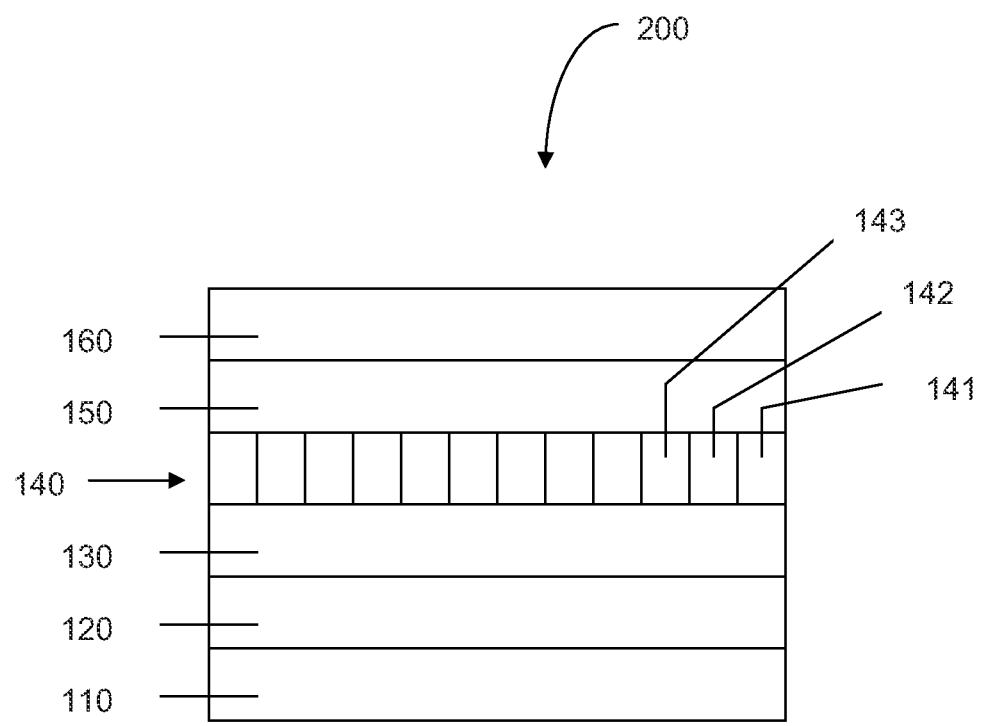
FIG. 2 includes another illustration of an organic light-emitting device.

In some embodiments, the photoactive layer is pixellated, as shown in FIG. 2. In device 200, layer 140 is divided into pixel or subpixel units 141, 142, and 143 which are repeated over the layer. Each of the pixel or subpixel units represents a different color. In some embodiments, the subpixel units are for red, green, and blue. Although three subpixel units are shown in the figure, two or more than three may be used.

In some embodiments, the different layers have the following range of thicknesses: anode 110, 500-5000 Å, in some embodiments, 1000-2000 Å; hole injection layer 120, 50-2000 Å, in some embodiments, 200-1000 Å; hole transport layer 130, 50-3000 Å, in some embodiments, 200-2000 Å; photoactive layer 140, 10-2000 Å, in some embodiments, 100-1000 Å; electron transport layer 150, 50-2000 Å, in some embodiments, 100-1000 Å; cathode 160, 200-10000 Å, in some embodiments, 300-5000 Å. The desired ratio of layer thicknesses will depend on the exact nature of the materials used. The location of the electron-hole recombination zone in the device, and thus the emission spectrum of the device, can be affected by the relative thickness of each layer. The desired ratio of layer thicknesses will depend on the exact nature of the materials used.

In some embodiments, the compounds having Formula II are useful as the emissive material in photoactive layer 140, having blue emission color. They can be used alone or as a dopant in a host material.

a. Photoactive Layer

In some embodiments, the photoactive layer comprises a host material and a compound having Formula II as a dopant. In some embodiments, a second host material may be present. In some embodiments, the photoactive layer consists essentially of a host material and a compound having Formula II as a dopant, wherein additional materials that would materially alter the characteristics or function of the layer are not present therein. In some embodiments, the photoactive layer consists essentially of a first host material, a second host material, and a compound having Formula II as a dopant, wherein additional materials that would materially alter the characteristics or function of the layer are not present therein. The weight ratio of dopant to total host material is in the range of 5:95 to 70:30; in some embodiments, 10:90 to 20:80.

In some embodiments, the host has a triplet energy level higher than that of the dopant, so that it does not quench the emission. In some embodiments, the host is selected from the group consisting of carbazoles, indolocarbazoles, triazines, aryl ketones, phenylpyridines, pyrimidines, phenanthrolines, triarylamines, (benzo)thiophenes, (benzo)furans, deuterated analogs thereof, combinations thereof, and mixtures thereof.

In some embodiments, the photoactive layer is intended to emit white light. In some embodiments, the photoactive layer comprises a host, a compound of Formula II, and one or more additional dopants emitting different colors, so that the overall emission is white. In some embodiments, the photoactive layer consists essentially of a host, a first dopant having Formula II, and a second dopant, where the second dopant emits a different color than the first dopant, wherein additional materials that would materially alter the characteristics or function of the layer are not present therein. In some embodiments, the emission color of the second dopant is yellow. In some embodiments, the photoactive layer consists essentially of a host, a first dopant having Formula II, a second dopant, and a third dopant, wherein additional materials that would materially alter the characteristics or function of the layer are not present therein. In some embodiments, the emission color of the second dopant is red and the emission color of the third dopant is green.

Any kind of electroluminescent ("EL") material can be used as second and third dopants. EL materials include, but are not limited to, small molecule organic fluorescent compounds, luminescent metal complexes, conjugated polymers, and mixtures thereof. Examples of fluorescent compounds include, but are not limited to, chrysenes, pyrenes, perylenes, rubrenes, coumarins, anthracenes, thiadiazoles, derivatives thereof, arylamino derivatives thereof, and mixtures thereof. Examples of metal complexes include, but are not limited to, metal chelated oxinoid compounds, such as tris(8-hydroxyquinolato)aluminum (Alq3); cyclometalated iridium and platinum electroluminescent compounds, such as complexes of iridium with phenylpyridine, phenylquinoline, or phenylpyrimidine ligands as disclosed in Petrov et al., U.S. Pat. No. 6,670,645 and Published PCT Applications WO 03/063555 and WO 2004/016710, and organometallic complexes described in, for example, Published PCT Applications WO 03/008424, WO 03/091688, and WO 03/040257, and mixtures thereof. Examples of conjugated polymers include, but are not limited to poly(phenylenevinylenes), polyfluorenes, poly(spirobifluorenes), polythiophenes, poly(p-phenylenes), copolymers thereof, and mixtures thereof.

Examples of red, orange and yellow light-emitting materials include, but are not limited to, complexes of Ir having phenylquinoline or phenylisoquinoline ligands, periflanthenes, fluoranthenes, and perylenes. Red light-emitting materials have been disclosed in, for example, U.S. Pat. No. 6,875,524, and published US application 2005-0158577.

In some embodiments, the second and third dopants are cyclometallated complexes of Ir or Pt.

b. Other Device Layers

The other layers in the device can be made of any materials which are known to be useful in such layers.

The anode 110 is an electrode that is particularly efficient for injecting positive charge carriers. It can be made of, for example materials containing a metal, mixed metal, alloy, metal oxide or mixed-metal oxide, or it can be a conducting polymer, and mixtures thereof. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material such as polyaniline as described in "Flexible light-emitting diodes made from soluble conducting polymer," Nature vol. 357, pp 477 479 (11 Jun. 1992). At least one of the anode and cathode should be at least partially transparent to allow the generated light to be observed.

The hole injection layer 120 comprises hole injection material and may have one or more functions in an organic electronic device, including but not limited to, planarization of the underlying layer, charge transport and/or charge injection properties, scavenging of impurities such as oxygen or metal ions, and other aspects to facilitate or to improve the performance of the organic electronic device. The hole injection layer can be formed with polymeric materials, such as polyaniline (PANI) or polyethylenedioxythiophene (PEDOT), which are often doped with protonic acids. The protonic acids can be, for example, poly(styrenesulfonic acid), poly(2-acrylamido-2-methyl-1-propanesulfonic acid), and the like.

The hole injection layer can comprise charge transfer compounds, and the like, such as copper phthalocyanine and the tetrathiafulvalene-tetracyanoquinodimethane system (TTF-TCNQ).

In some embodiments, the hole injection layer comprises at least one electrically conductive polymer and at least one fluorinated acid polymer.

In some embodiments, the hole injection layer is made from an aqueous dispersion of an electrically conducting polymer doped with a colloid-forming polymeric acid. Such materials have been described in, for example, published U.S. patent applications US 2004/0102577, US 2004/0127637, US 2005/0205860, and published PCT application WO 2009/018009.

Examples of hole transport materials for layer 130 have been summarized for example, in Kirk-Othmer Encyclopedia of Chemical Technology, Fourth Edition, Vol. 18, p. 837-860, 1996, by Y. Wang. Both hole transporting molecules and polymers can be used. Commonly used hole transporting molecules are: N,N'-diphenyl-N,N'-bis(3-methylphenyl)-[1,1'-biphenyl]-4,4'-diamine (TPD), 1,1-bis[(di-4-tolylamino)phenyl]cyclohexane (TAPC), N,N'-bis(4-methylphenyl)-N,N'-bis(4-ethylphenyl)-[1,1'-(3,3'-dimethyl) biphenyl]-4,4'-diamine (ETPD), tetrakis-(3-methylphenyl)-N,N,N',N'-2,5-phenylenediamine (PDA), a-phenyl-4-N,N-diphenylaminostyrene (TPS), p-(diethylamino) benzaldehyde diphenylhydrazone (DEH), triphenylamine (TPA), bis[4-(N,N-diethylamino)-2-methylphenyl](4-methylphenyl)methane (MPMP), 1-phenyl-3-[p-(diethylamino) styryl]-5-[p-(diethylamino)phenyl]pyrazoline (PPR or DEASP), 1,2-trans-bis(9H-carbazol-9-yl)cyclobutane (DCZB), N,N,N',N'-tetrakis(4-methylphenyl)-(1,1'-biphenyl)-4,4'-diamine (TTB), N,N'-bis(naphthalen-1-yl)-N,N'-bis-(phenyl)benzidine (—NPB), and porphyrinic compounds, such as copper phthalocyanine. In some embodiments, the hole transport layer comprises a hole transport polymer. In some embodiments, the hole transport polymer is a distyrylaryl compound. In some embodiments, the aryl group has two or more fused aromatic rings. In some embodiments, the aryl group is an acene. The term "acene" as used herein refers to a hydrocarbon parent component that contains two or more ortho-fused benzene rings in a straight linear arrangement. Other commonly used hole transporting polymers are polyvinylcarbazole, (phenylmethyl)-polysilane, and polyaniline. It is also possible to obtain hole transporting polymers by doping hole transporting molecules such as those mentioned above into polymers such as polystyrene and polycarbonate. In some cases, triarylamine polymers are used, especially triarylamine-fluorene copolymers. In some cases, the polymers and copolymers are crosslinkable.

In some embodiments, the hole transport layer further comprises a p-dopant. In some embodiments, the hole transport layer is doped with a p-dopant. Examples of p-dopants include, but are not limited to, tetrafluorotetracyanoquinodimethane (F4-TCNQ) and perylene-3,4,9,10-tetracarboxylic-3,4,9,10-dianhydride (PTCDA).

Examples of electron transport materials which can be used for layer 150 include, but are not limited to, metal chelated oxinoid compounds, including metal quinolate derivatives such as tris(8-hydroxyquinolato)aluminum (AlQ), bis(2-methyl-8-quinolinolato)(p-phenylphenolato) aluminum (BAlq), tetrakis-(8-hydroxyquinolato)hafnium (HfQ) and tetrakis-(8-hydroxyquinolato)zirconium (ZrQ); and azole compounds such as 2-(4-biphenylyl)-5-(4-t-butylphenyl)-1,3,4-oxadiazole (PBD), 3-(4-biphenylyl)-4-phenyl-5-(4-t-butylphenyl)-1,2,4-triazole (TAZ), and 1,3,5-tri (phenyl-2-benzimidazole)benzene (TPBI); quinoxaline derivatives such as 2,3-bis(4-fluorophenyl)quinoxaline; phenanthrolines such as 4,7-diphenyl-1,10-phenanthroline (DPA) and 2,9-dimethyl-4,7-diphenyl-1,10-phenanthroline (DDPA); and mixtures thereof. In some embodiments, the electron transport layer further comprises an n-dopant. N-dopant materials are well known. The n-dopants include, but are not limited to, Group 1 and 2 metals; Group 1 and 2 metal salts, such as LiF, CsF, and $Cs_2CO_3$; Group 1 and 2 metal organic compounds, such as Li quinolate; and molecular n-dopants, such as leuco dyes, metal complexes, such as $W_2(hpp)_4$ where hpp=1,3,4,6,7,8-hexahydro-2H-pyrimido-[1,2-a]-pyrimidine and cobaltocene, tetrathianaphthacene, bis(ethylenedithio)tetrathiafulvalene, heterocyclic radicals or diradicals, and the dimers, oligomers, polymers, dispiro compounds and polycycles of heterocyclic radical or diradicals.

An anti-quenching layer may be present between the photoactive layer and the electron transport layer to prevent quenching of blue luminance by the electron transport layer. To prevent energy transfer quenching, the triplet energy of the anti-quenching material has to be higher than the triplet energy of the blue emitter. To prevent electron transfer quenching, the LUMO level of the anti-quenching material has to be shallow enough (with respect to the vacuum level) such that electron transfer between the emitter exciton and the anti-quenching material is endothermic. Furthermore, the HOMO level of the anti-quenching material has to be deep enough (with respect to the vacuum level) such that electron transfer between the emitter exciton and the anti-quenching material is endothermic. In general, anti-quenching material is a large band-gap material with high triplet energy.

Examples of materials for the anti-quenching layer include, but are not limited to, triphenylene, triphenylene derivatives, carbazole, carbazole derivatives, and deuterated analogs thereof. Some specific materials include those shown below.

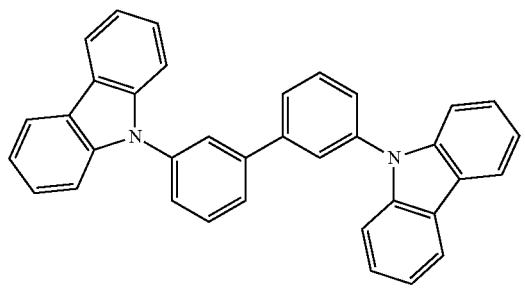

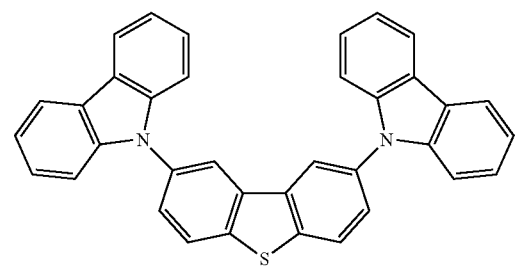

-continued

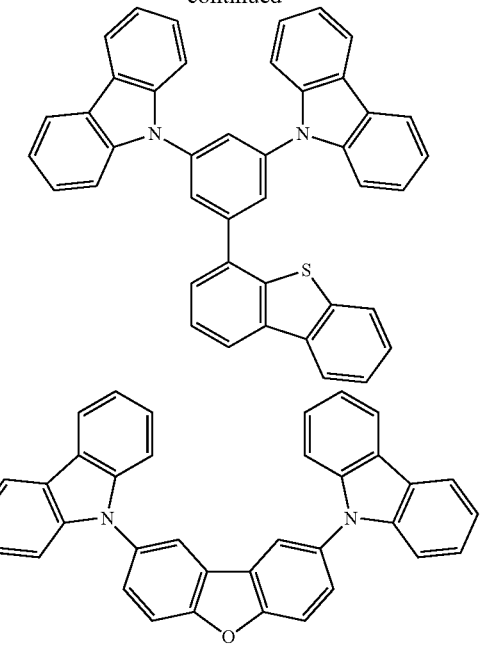

An optional electron injection layer may be deposited over the electron transport layer. Examples of electron injection materials include, but are not limited to, Li-containing organometallic compounds, LiF, $Li_2O$, Li quinolate, Cs-containing organometallic compounds, CsF, $Cs_2O$, and $Cs_2CO_3$. This layer may react with the underlying electron transport layer, the overlying cathode, or both. When an electron injection layer is present, the amount of material deposited is generally in the range of 1-100 Å, in some embodiments 1-10 Å.

The cathode 160, is an electrode that is particularly efficient for injecting electrons or negative charge carriers. The cathode can be any metal or nonmetal having a lower work function than the anode. Materials for the cathode can be selected from alkali metals of Group 1 (e.g., Li, Cs), the Group 2 (alkaline earth) metals, the Group 12 metals, including the rare earth elements and lanthanides, and the actinides. Materials such as aluminum, indium, calcium, barium, samarium and magnesium, as well as combinations, can be used.

It is known to have other layers in organic electronic devices. For example, there can be a layer (not shown) between the anode 110 and hole injection layer 120 to control the amount of positive charge injected and/or to provide band-gap matching of the layers, or to function as a protective layer. Layers that are known in the art can be used, such as copper phthalocyanine, silicon oxy-nitride, fluorocarbons, silanes, or an ultra-thin layer of a metal, such as Pt. Alternatively, some or all of anode layer 110, active layers 120, 130, 140, and 150, or cathode layer 160, can be surface-treated to increase charge carrier transport efficiency. The choice of materials for each of the component layers is preferably determined by balancing the positive and negative charges in the emitter layer to provide a device with high electroluminescence efficiency.

It is understood that each functional layer can be made up of more than one layer.

c. Device Fabrication

The device layers can be formed by any deposition technique, or combinations of techniques, including vapor deposition, liquid deposition, and thermal transfer.

In some embodiments, the device is fabricated by liquid deposition of the hole injection layer, the hole transport layer, and the photoactive layer, and by vapor deposition of the anode, the electron transport layer, an electron injection layer and the cathode.

The hole injection layer can be deposited from any liquid medium in which it is dissolved or dispersed and from which it will form a film. In one embodiment, the liquid medium consists essentially of one or more organic solvents wherein additional materials that would materially alter the characteristics or function of the liquid medium are not present therein. In one embodiment, the liquid medium consists essentially of water or water and an organic solvent, wherein additional materials that would materially alter the characteristics or function of the liquid medium are not present therein. The hole injection material can be present in the liquid medium in an amount from 0.5 to 10 percent by weight. The hole injection layer can be applied by any continuous or discontinuous liquid deposition technique. In one embodiment, the hole injection layer is applied by spin coating. In one embodiment, the hole injection layer is applied by ink jet printing. In one embodiment, the hole injection layer is applied by continuous nozzle printing. In one embodiment, the hole injection layer is applied by slot-die coating. After liquid deposition, the liquid medium can be removed in air, in an inert atmosphere, or by vacuum, at room temperature or with heating.

The hole transport layer can be deposited from any liquid medium in which it is dissolved or dispersed and from which it will form a film. In one embodiment, the liquid medium consists essentially of one or more organic solvents, wherein additional materials that would materially alter the characteristics or function of the liquid medium are not present therein. In one embodiment, the liquid medium consists essentially of water or water and an organic solvent, wherein additional materials that would materially alter the characteristics or function of the liquid medium are not present therein. In one embodiment the organic solvent is an aromatic solvent. In one embodiment, the organic liquid is selected from chloroform, dichloromethane, chlorobenzene, dichlorobenzene, toluene, xylene, mesitylene, anisole, and mixtures thereof. The hole transport material can be present in the liquid medium in a concentration of 0.2 to 2 percent by weight. The hole transport layer can be applied by any continuous or discontinuous liquid deposition technique. In one embodiment, the hole transport layer is applied by spin coating. In one embodiment, the hole transport layer is applied by ink jet printing. In one embodiment, the hole transport layer is applied by continuous nozzle printing. In one embodiment, the hole transport layer is applied by slot-die coating. After liquid deposition, the liquid medium can be removed in air, in an inert atmosphere, or by vacuum, at room temperature or with heating.

The photoactive layer can be deposited from any liquid medium in which it is dissolved or dispersed and from which it will form a film. In one embodiment, the liquid medium consists essentially of one or more organic solvents, wherein additional materials that would materially alter the characteristics or function of the liquid medium are not present therein. In one embodiment, the liquid medium consists essentially of water or water and an organic solvent, wherein additional materials that would materially alter the characteristics or function of the liquid medium are not present therein. In one embodiment the organic solvent is an aromatic solvent. In one embodiment, the organic solvent is selected from chloroform, dichloromethane, toluene, anisole, 2-butanone, 3-pentanone, butyl acetate, acetone, xylene, mesitylene, chlorobenzene, tetrahydrofuran, diethyl ether, trifluorotoluene, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. In one embodiment, the photoactive layer is applied by continuous nozzle printing. In one embodiment, the photoactive layer is applied by slot-die coating. After liquid deposition, the liquid medium can be removed in air, in an inert atmosphere, or by vacuum, at room temperature or with heating.

The electron transport layer can be deposited by any vapor deposition method. In one embodiment, it is deposited by thermal evaporation under vacuum.

The electron injection layer can be deposited by any vapor deposition method. In one embodiment, it is deposited by thermal evaporation under vacuum.

The cathode can be deposited by any vapor deposition method. In one embodiment, it is deposited by thermal evaporation under vacuum.

EXAMPLES

The concepts described herein will be further described in the following examples, which do not limit the scope of the invention described in the claims.

Synthesis Example 1

This example illustrates the synthesis of Compound L1 and Compound B1.

The synthesis was carried out in nine steps as follows:

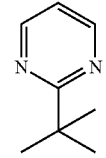

Step 1: Synthesis of 2-tert-Butylpyrimidine 1,1,3,3-Tetramethoxypropane was sparged with $N_2$ for ~5 minutes. Under nitrogen, a 50-mL Schlenk tube was charged with 1,1,3,3-tetramethoxypropane (23.5 g, 143 mmol) and pivalamidine hydrochloride (10.2 g, 75.0 mmol). The viscous mixture was stirred and heated at 195° C. for 3.5 h. The reaction was black. The solvent level appeared to have diminished by ~20-30%. From the reaction mixture, about 15 g of a mixture of dark brown oil and sludge was obtained and transferred to an Erlenmeyer flask by dichloromethane and a small amount of methanol. There was a significant amount of sludge that was dissolved by stirring in dichloromethane. Triethylamine (1 mL) was added to the mixture. The mixture was passed through a plug of silica (150 g), rinsed with dichloromethane (1 L), and concentrated under reduced pressure to give 9.4 g of a brown liquid. The product was purified by vacuum distillation to give a clear colorless liquid (5.2 g, 51%). $^1$H NMR ($CD_2Cl_2$, 499.8 MHz) δ 8.67 (d, J=4.8 Hz, 2H), 7.09 (t, J=4.8 Hz, 1H), 1.40 (s, 9H).

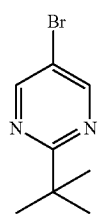

Step 2: Synthesis of 5-Bromo-2-tert-butylpyrimidine 2-tert-Butylpyrimidine (5.20 g, 38.2 mmol), acetic acid (20 mL), and sodium acetate (3.76 g, 45.8 mmol) were charged to a 4-neck, 250-mL round-bottom flask equipped with a stir bar, a condenser, an addition funnel, N$_2$ bubbler, and 2 stoppers. Bromine (2.35 mL, 45.9 mmol) in 5 mL of acetic acid was added to addition funnel. The aluminum heating mantle was set to 85° C. When the internal reaction temperature was 70° C., bromine was added dropwise. After addition was finished, the internal temperature was adjusted to 78° C. The reaction was monitored by TLC. After 6.5 h, the reaction was quenched with 10% aqueous sodium bisulfite (15 mL), diluted with water (175 mL), and transferred to an Erlenmeyer flask. The mixture was cooled by an ice/water bath and neutralized with 10% aqueous sodium carbonate. After continued cooling and diluting with water, the total volume was about 600 mL. The white solid was filtered, washed with water and dried on filter paper to give 5.6 g of a white solid. The solid was suspended in 100 mL of dilute aqueous sodium bicarbonate. The mixture was stirred and heated with heating mantle under N$_2$ until the solid melted. The heat source was removed, and the stirring was continued during cooling. The mixture was then stirred at room temperature for 2 h. The solid was filtered, rinsed with water twice, and dried on frit to give a white solid (4.3 g, 52%). $^1$H NMR (CD$_2$Cl$_2$, 499.8 MHz) δ 8.72 (s, 2H), 1.39 (s, 9H).

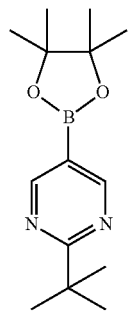

Step 3: Synthesis of 2-tert-Butyl-5-(4,4,5,5-tetramethyl-1,3,2-dioxaborolan-2-yl)pyrimidine Inside a glovebox, a 2-neck 50-mL round-bottom flask equipped with a stir bar and rubber septum was charged with 5-bromo-2-tert-butylpyrimidine (4.20 g, 19.5 mmol), bis(pinacolato)diboron (5.45 g, 21.5 mmol), Pd(dba)$_2$ (0.34 g, 0.59 mmol), tricyclohexylphosphine (0.33 g, 1.2 mmol) and potassium acetate (2.90 g, 29.5 mmol). The flask was capped and removed from the dry box. The cap was removed; a condenser and N$_2$ bubbler were quickly placed on the flask. 1,4-Dioxane (100 mL) was added via cannula transfer. The aluminum heating mantle was set at 105° C., and the reaction was stirred for 15.5 h. The reaction mixture was diluted with EtOAc, passed through a plug of Celite®, rinsed with EtOAc, and concentrated under reduced pressure to give 7.7 g orange waxy solid. Under N$_2$, the crude product was dissolved in 80 mL of boiling MeOH. The solution was filtered while still hot. The mixture was placed in a round-bottom flask and capped. After cooling to room temperature, crystals began to form. After ~1 hour, the mixture was stored in a refrigerator. After 1 day, the crystals were filtered, rinsed with 20 mL of cold MeOH, and dried under high vacuum to give a white solid (3.8 g, 75%). $^1$H NMR (CD$_2$Cl$_2$, 499.8 MHz) δ 8.91 (5, 2H), 1.40 (5, 9H), 1.36 (5, 12H).

Step 4: Synthesis of 2-(2-Bromophenyl-[1,3,4]oxadiazole

A 500-mL round-bottom flask equipped with a stir bar, condenser, and N$_2$ bubbler was charged with 2-bromobenzohydrazide (25.4 g, 118 mmol) and triethyl orthoformate (85.0 g, 574 mmol). The mixture was stirred and heated under N$_2$ at 160° C. for 21 h. The mixture was then concentrated under reduced pressure to give an oil. Ethyl acetate was added to the oil and washed with 1N aqueous HCl twice, then brine. The organic layer was separated, dried over MgSO$_4$, filtered, concentrated under reduced pressure to give 21.8 g of a light brown oil. The crude product was dissolved in CH$_2$Cl$_2$, passed through a plug of silica (160 g), rinsed with CH$_2$Cl$_2$ then 2% EtOAc/CH$_2$Cl$_2$. The filtrate was concentrated under reduced pressure to give a colorless oil (20 g, 75%). $^1$H NMR (CD$_2$Cl$_2$, 499.8 MHz) δ 8.56 (m, 1H, triazole-H), 7.89 (dd, J=1.7, 7.8 Hz, 1H, C6-H), 7.67 (dd, J=1.1, 8.0 Hz, 1H, C3-H), 7.48 (dt, J=1.2, 7.6 Hz, 1H, C4-H), 7.41 (dt, J=1.7, 7.8 Hz, 1H, C5-H).

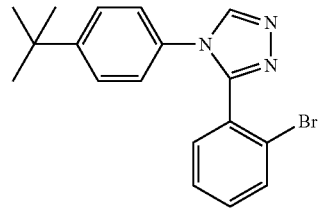 [SMILES: CC(C)(C)c1ccc(-n2cnnc2-c2ccccc2Br)cc1]

Step 5: Synthesis of 3-(2-Bromophenyl)-4-(4-t-butylphenyl)-4H-[1,2,4]triazole A 100-mL round-bottom flask equipped with a stir bar, condenser and N$_2$ bubbler was charged with 2-(2-bromophenyl)[1,3,4]oxadiazole (5.00 g, 22.2 mmol), 4-tert-butylaniline (3.54 mL, 22.2 mmol), and o-dichlorobenzene (24 mL). Trifluoroacetic acid (1.70 mL, 22.2 mmol) was then added. The heating block was set to 185° C. and the reaction mixture was stirred for 15 h. Aqueous Na$_2$CO$_3$ (10%) was added to the reaction mixture until pH ~9 was obtained. The product was extracted twice with CH$_2$Cl$_2$. The combined organic layers were washed with brine, dried over MgSO$_4$, and concentrated under reduced pressure to give about 12 g light orange semisolid. The product was purified by automated column chromatography on a Biotage® 340-g KP-Sil™ cartridge to give a white solid (4.9 g, 62%). $^1$H NMR (CD$_2$Cl$_2$, 499.8 MHz) δ 8.41 (s, 1H, triazole-H), 7.62 (m, 1H), 7.49 (dd, J=1.7, 7.6 Hz, 1H), 7.45-7.35 (m, 4H), 7.13-7.09 (m, 2H), 1.31 (s, 9H).

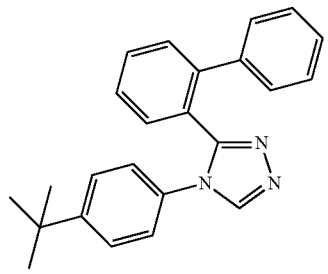 [SMILES: CC(C)(C)c1ccc(-n2cnnc2-c2ccccc2-c2ccccc2)cc1]

Step 6: Synthesis of 3-Biphenyl-2-yl-4-(4-tert-butylphenyl)I-4H-[1,2,4]triazole

A 500-mL, 2-neck round-bottom flask equipped with a stir bar, condenser, N$_2$ bubbler and N$_2$ sparge tube, was charged with phenyl-boronic acid (3.25 g, 26.7 mmol), 3-(2-bromophenyl)-4-(4-t-butylphenyl)-4H-[1,2,4]triazole (4.75 g, 13.3 mmol), toluene (120 mL), and K$_3$PO$_4$ monohydrate (9.21 g, 40.0 mmol). The mixture was sparged with N$_2$ for 40 minutes. In a glovebox, Pd$_2$(dba)$_3$ (0.305 g, 0.330 mmol), S-Phos (0.547 g, 1.33 mmol) and toluene (35 mL) were combined in round-bottom flask and stirred for 10 min. The flask was removed from the glovebox, and the catalyst solution was transferred to the reaction flask via cannula. The heating block was set to 140° C. and the reaction was stirred at this temperature for 16 h. The mixture was then allowed to cool to room temperature and CH$_2$Cl$_2$ (200 mL) was added. The mixture was passed through a plug of silica (80 g) and rinsed with dichloromethane and then ethyl acetate. The filtrate was concentrated under reduced pressure to give a viscous orange oil (5.35 g). The crude product was purified by automated flash column chromatography on a Biotage® 340-g KP-Sil™ cartridge to give a yellow foamy solid (3.4 g, 72%). $^1$H NMR (CD$_2$Cl$_2$, 499.8 MHz) δ 8.13 (s, 1H, triazole-H), 7.83 (m, 1H), 7.56 (m, 2H), 7.29 (m, 1H), 7.17 (tt, J=1.2, 7.4 Hz, 1H), 7.10-7.03 (m, 4H), 6.62-6.60 (m, 2H), 6.32-6.30 (m, 2H), 1.29 (s, 9H).

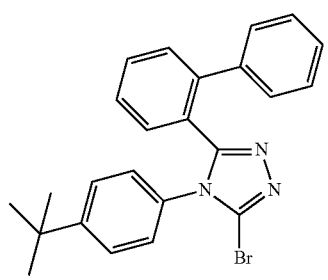 [SMILES: CC(C)(C)c1ccc(-n2c(Br)nnc2-c2ccccc2-c2ccccc2)cc1]

Step 7: Synthesis of 3-Biphenyl-2-yl-5-bromo-4-(4-tert-butylphenyl)-4H-[1,2,4]triazole A 300-mL round-bottom flask equipped with a stir bar, condenser and N$_2$ bubbler was charged with 3-biphenyl-2-yl-4-(4-tert-butylphenyl)I-4H-[1,2,4]triazole (3.4 g, 9.6 mmol), N-bromosuccinimide (2.1 g, 12 mmol), and 40 mL of 1:1 carbon tetrachloride:acetic acid. The aluminum heating mantle was set at 120° C., and the reaction mixture was stirred for 4.5 h. The reaction mixture was transferred to an Erlenmeyer flask. Aqueous sodium carbonate (10%) was added and the mixture was transferred to a separatory funnel. The product was extracted twice with CH$_2$Cl$_2$, washed with water and then brine. It was concentrated under reduced pressure to give 4.45 g of a light orange foamy solid. The product was purified by automated flash column chromatography to give a white solid (2.4 g, 58%). $^1$H NMR (CD$_2$Cl$_2$, 499.8 MHz) δ 7.74 (m, 1H), 7.55 (m, 1H), 7.51 (m, 1H), 7.28-7.25 (m, 2H), 7.19-7.15 (m, 2H), 7.11-7.08 (m, 2H), 6.72-6.74 (m, 2H), 6.27-6.24 (m, 2H), 1.30 (s, 9H).

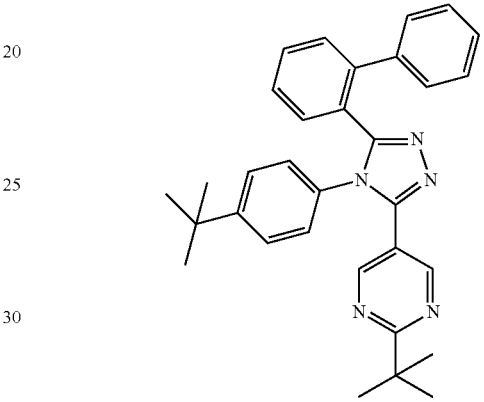

Step 8: Synthesis of 5-[5-Biphenyl-2-yl-4-(4-tert-butylphenyl)-4H-[1,2,4]triazol-3-yl]-2-tert-butylpyrimidine, Compound L1

A 2-neck 250-mL round-bottom flask equipped with a stir bar, condenser, N$_2$ bubbler and sparge tube was charged with 2-tert-butyl-5-(4,4,5,5-tetramethyl-[1,2,3]dioxaborolan-2-yl)-pyrimidine (1.4 g, 5.3 mmol), 3-biphenyl-2-yl-5-bromo-4-(4-tert-butylphenyl)-4H-[1,2,4]triazole (1.5 g, 3.7 mmol), and Cs$_2$CO$_3$ (2.3 g, 7.1 mmol). 1,4-Dioxane (14 mL) and water (1 mL) were added. The solution was sparged with N$_2$ for 30 min, then the sparge tube was removed and quickly replaced with a rubber septum. In the glovebox, Pd$_2$(dba)$_3$ (0.16 g, 0.17 mmol), S-phos (0.28 g, 0.68 mmol) were combined with 1,4-dioxane (5 mL) in a 100-mL round-bottom flask. The flask was sealed with a rubber septum. The mixture was stirred for 20 min, and then removed from dry box. The catalyst solution was transferred to the reaction flask via a cannula. The aluminum heating mantle was set to 90° C. and the mixture was stirred for 3.5 h. The mixture was then concentrated under reduced pressure to give an orange oil, which was then transferred to a separatory funnel with EtOAc and water. The organic layer was washed with water and then brine, dried over MgSO$_4$, and concentrated under reduced pressure to give 0.7 g of an orange viscous oil. The produced was purified by automated flash column chromatography on a 50-g Biotage® KP-Sil™ cartridge with a liquid load from a minimal amount of CH$_2$Cl$_2$ to give a white solid (1.3 g, 76%). $^1$H NMR (CD$_2$Cl$_2$, 499.8 MHz) δ 8.62 (s, 2H, pyrimidine-H), 7.79 (m, 1H), 7.58-7.51 (m, 2H), 7.30 (m, 1H), 7.20 (m, 1H), 7.15-7.12 (m, 2H), 7.05 (d, J=8.8 Hz, 2H), 6.78-6.76 (m, 2H), 6.16 (d, 2H), 1.35 (s, 9H), 1.29 (s, 9H). LC/MS (SQ with ESI) $C_{32}H_{33}N_5$ calcd: 488.28 ([M+H]+). Found: 488.44. UPLC purity: 98.63%.

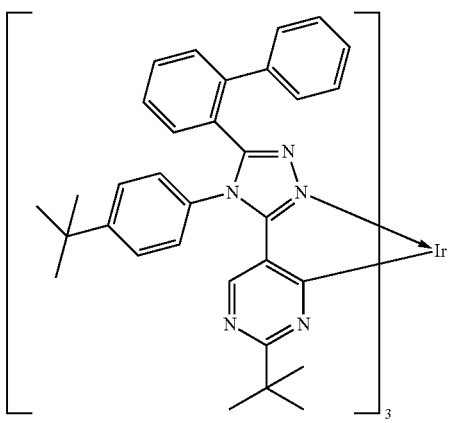

Step 9: Synthesis of Tris{5-[5-(biphenyl-2-yl)-4-(4-tert-butylphenyl)-4H-1,2,4-triazol-3-yl-kN$^2$]-2-tert-butylpyrimidin-4-yl-kC$^4$}iridium, Compound B1

A 20-mL vial was charged with iridium acetylacetonate (0.38 g, 0.78 mmol) and 5-[5-biphenyl-2-yl-4-(4-tert-butylphenyl)-4H-[1,2,4]triazol-3-yl]-2-tert-butylpyrimidine (1.2 g, 2.5 mmol). The content was mixed and transferred a 7-mL pressure tube and sealed under $N_2$. The tube was heated 250° C. for 48 h. The crude product purified by automated flash column chromatography on a 100-g Biotage® KP-Sil™ cartridge. Then the product was suspended in 75-100 mL of hexanes, stirred under $N_2$, and heated briefly to reflux. The product formed a light powder and remained largely insoluble. The mixture was allowed to cool to room temperature, and then concentrated under reduced pressure to a volume of 25-30 mL. The solid was filtered, rinsed with minimal hexanes, and dried under high vacuum to give a yellow powder (0.38 g, 35%). $^1$H NMR (CD$_2$Cl$_2$, 500 MHz) δ 7.92 (d, J=7.4 Hz, 3H, ArH), 7.53 (m, 6H, ArH), 7.44 (5, 3H, ArH), 7.29 (d, J=7.4 Hz, 3H, ArH), 7.16-7.08 (m, 6H, ArH), 6.95 (br, 3H, ArH), 6.80-6.45 (m, 15H, ArH), 6.19 (br, 3H, ArH), 1.29 (s, 27H, C(CH$_3$)$_3$), 1.06 (5, 27H, C(CH$_3$)$_3$. 173.6, 159.0, 154.6, 152.5, 144.9, 141.8, 139.3, 132.4, 130.8, 130.2, 129.8, 128.4 (5), 128.4, 127.3, 127.2, 126.3, 126.0, 125.9, 125.6, 125.2, 38.9, 34.6, 30.9, 29.5. LC/MS (SQD with ESI) $C_{96}H_{96}IrN_{15}$ calcd: 1652.77 ([M+H]+). Found: 1652.12. LC purity 99.14%.

Synthesis Example 2

This example illustrates the synthesis of Compound L2 and Compound B2.
The synthesis was carried out in four steps as follows:

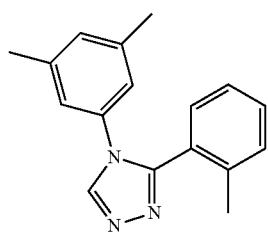 [SMILES: Cc1cc(C)cc(-n2cnnc2-c2ccccc2C)c1]

Step 1: Synthesis of 4-(3,5-Dimethylphenyl)-3-o-tolyl-4H-[1,2,4]triazole 2-o-Tolyl-[1,3,4]oxadiazole (4.0 g, 25 mmol), 3,5-dimethylaniline (3.1 mL, 25 mmol), and o-dichlorobenzene (25 mL) were charged into a 200-mL round-bottom flask equipped with a stir bar, condenser and $N_2$ bubbler. Trifluoroacetic acid (1.9 mL) was then added to give a clear solution. The flask was placed in an aluminum heating mantle set at 182° C. The reaction mixture became cloudy. It was stirred overnight. TLC showed that the starting materials were mostly consumed. The reaction mixture was transferred to a separatory funnel and partitioned between dichloromethane and water. The organic layer was separated, washed with brine, dried over MgSO$_4$, filtered, and concentrated under reduced pressure to give ~8 g of an oily reside with suspended particles. The mixture was suspended in dichloromethane (20 mL) and filtered through a 0.54 micron PTFE filter. The product was purified by on a 340-g Biotage® KP-Sil™ cartridge to give a colorless powder (3.15 g, 48%). $^1$H NMR (CD$_2$Cl$_2$, 500 MHz, reference CH$_2$Cl$_2$ δ 5.33) δ 8.37 (s, 1H, triazole C5-H), 7.35 (dt, J=1.6, 7.5 Hz, 1H, ArH), 7.26-7.22 (m, 2H, ArH), 7.19 (m, 1H, ArH), 7.01 (m, 1H, ArH), 6.72 (m, 2H, ArH), 2.24 (br, 6H, Ar(CH$_3$)$_2$), 2.14 (s, 3H, ArCH$_3$). $^{13}$C NMR (CD$_2$Cl$_2$, 126 MHz, ref. CH2Cl2 δ 54.24) δ 153.7, 144.4, 140.4, 139.0, 135.0, 131.4, 131.2, 131.0, 130.7, 127.6, 126.4, 123.1, 21.6, 20.5.

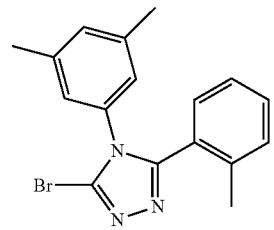 [SMILES: Cc1cc(C)cc(-n2c(Br)nnc2-c2ccccc2C)c1]

Step 2: Synthesis of 3-Bromo-4-(3,5-dimethylphenyl)-5-o-tolyl-4H[1,2,4]triazole 4-(3,5-Dimethylphenyl)-3-o-tolyl-4H-[1,2,4]triazole (3.0 g, 11 mmol) was charged to an oven-dried 250-mL round-bottom flask equipped with a stir bar, thermometer $N_2$ bubbler and rubber septum. THF (120 mL) was added via cannula. The flask was placed in a dry ice/acetone bath. When internal temperature reached <70° C., n-BuLi (2.5 M in hexanes, 4.7 mL, 12 mmol) was added dropwise via cannula over ~10 min while maintaining the internal temperature below −67° C. This mixture was stirred for about 40 min. Bromine (0.60 mL, 12 mmol) was added via syringe dropwise while maintaining the internal temperature below −67° C. The reaction mixture was stirred at this temperature for 40 min, during which the starting material was almost fully consumed. The cooling bath was then removed.

After a few minutes, about 5-10 mL of 10% aqueous sodium bisulfite and approximately 75 mL of water were added. The mixture was transferred to a separatory funnel and partitioned between EtOAc and water. The organic layers were combined, washed with brine, dried over MgSO$_4$, filtered, and concentrated under reduced pressure to give 4 g of a colorless solid, which was eluted through a 150-g silica gel plug with 750 mL of a 3:1 dichloromethane: EtOAc mixture to give a colorless solid (3.59 g, 92%). $^1$H NMR (CD$_2$Cl$_2$, 500 MHz, reference CH$_2$Cl$_2$ δ 5.33) δ 7.31 (m, 1H, ArH), 7.23 (m, 1H, ArH), 7.17-7.12 (m, 2H, ArH), 7.07 (m, 1H, ArH), 6.76 (m, 2H, ArH), 2.28 (br, 6H, ArCH$_3$), 2.24 (s, 6H, ArCH$_3$). $^{13}$C NMR (CD$_2$Cl$_2$, 126 MHz, ref. CH2Cl2 δ 54.24) δ 156.8, 140.4, 139.1, 134.3, 132.2, 131.3, 131.2, 130.9, 130.8, 127.3, 126.2, 125.7, 21.6, 20.6.

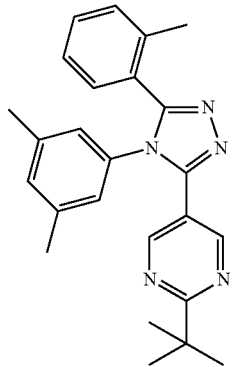 [SMILES: Cc1cc(C)cc(-n2c(-c3cnc(C(C)(C)C)nc3)nnc2-c2ccccc2C)c1]

Step 3: Synthesis of 2-tert-Butyl-5-[4-(3,5-dimethylphenyl)-5-o-tolyl-4H-[1,2,4]triazol-3-yl]pyrimidine, Compound L2

3-Bromo-4-(3,5-dimethylphenyl)-5-o-tolyl-4H[1,2,4]triazole (1.1 g, 3.2 mmol), 2-tert-butyl-5-(4,4,5,5-tetramethyl-[1,2,3]dioxaborolan-2-yl)pyrimidine (0.97 g, 3.7 mmol), and Cs$_2$CO$_3$ (2.4 g, 7.4 mmol) were charged into a 2-neck 200-mL round-bottom flask equipped with a stir bar, condenser, N$_2$ bubbler and sparge tube. 1,4-Dioxane (40 mL) and water (3 mL) were added. The solution was sparged with N$_2$ for 30 min, then the sparge tube was replaced with a rubber septum. In a glovebox, Pd$_2$(dba)$_3$ (0.088 g, 0.096 mmol), S-phos (0.16 g, 0.39 mmol), and 1,4-dioxane (20 mL) were charged into a 100-mL round-bottom flask. The flask was sealed with a rubber septum, and the mixture was stirred for 20 min. The catalyst solution was transferred to the reaction flask via cannula. The aluminum heating mantle was set at 100° C. and the mixture was stirred for 15.5 h.

After full conversion was observed by TLC, the mixture was allowed to cool, transferred to a 500-mL round-bottom flask, and concentrated under reduced pressure. The residue was transferred to a separatory funnel and partitioned between dichloromethane and water. The organic layer was separated, washed with brine, dried over MgSO$_4$, filtered, and concentrated under reduced pressure to give 1.8 g of a viscous orange oil. The product was purified by automated flash column chromatography on a 100-g Biotage® KP-Sil™ cartridge to give 1.1 g of a colorless foamy solid, which was suspended in hexanes (200 mL). The mixture was concentrated to ~25 mL and allowed to cool in a refrigerator. The solid was filtered, rinsed with cold hexanes (~25 mL), and placed under reduced pressure to give a colorless powder (0.90 g, 70%). $^1$H NMR (CD$_2$Cl$_2$, 500 MHz, reference CH$_2$Cl$_2$ δ 5.33) δ 8.73 (s, 2H, pyrimidineC-H), 7.32 (dt, J=1.6, 7.3 Hz, 1H, ArH), 7.26 (m, 1H, ArH), 7.20-7.13 (m, 2H, ArH), 7.06 (m, 1H, ArH), 6.72 (m, 2H, ArH), 2.28 (s, 3H, ArCH$_3$), 2.23 (br, 6H, Ar(CH$_3$)$_2$), 1.38 (s, 9H, C(CH$_3$)$_3$). $^{13}$C NMR (CD$_2$Cl$_2$, 126 MHz, ref. CH2Cl2 δ 54.24) δ178.6, 156.3, 156.0, 150.4, 141.0, 139.4, 134.8, 132.3, 131.5, 131.2, 130.8, 127.3, 126.2, 125.6, 119.7, 40.3, 30.0, 21.6, 20.8.

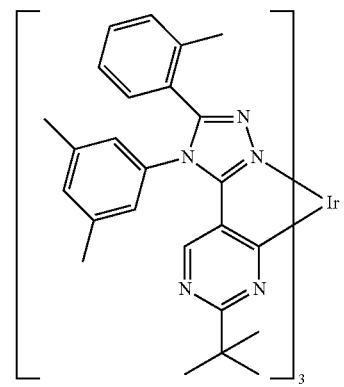

Step 4: Synthesis of Tris{2-tert-butyl-5-[4-(3,5-dimethylphenyl)-5-(2-methylphenyl)-4H-1,2,4-triazol-3-yl-κN$^2$]pyrimidin-4-yl-κC$^4$}iridium, Compound B2

Inside a glovebox, iridium acetylacetonate (0.31 g, 0.63 mmol) and 2-tert-butyl-5-[4-(3,5-dimethylphenyl)-5-o-tolyl-4H-[1,2,4]triazol-3-yl]-pyrimidine (0.85 g, 2.1 mmol) were charged into a 7-ml pressure tube. The tube was sealed in a glovebox to a reactor head. The reaction mixture was heated at 250° C. for 51 h. The crude mixture was rinsed from the tube with CH$_2$Cl$_2$ and concentrated under reduced pressure to give a brown oil (~1 g). The crude product was purified by automated flash column chromatography on a 50-g Biotage® KP-Sil® cartridge with a liquid load from dichloromethane. The chromatography separated the higher Rf impurities, but the ligand and product coeluted. These fractions were concentrated and dried under reduced pressure to give a glassy brown solid (~400 mg), which was then dissolved in EtOAc (4 mL) inside a 50 mL round-bottom flask. The solution was heated to reflux and stirred under nitrogen atmosphere. Hexanes (4 mL) were added to the boiling solution, which became cloudy. More hexanes (12 mL) were added. The stir bar was removed, and the flask was capped and allowed to cool overnight.

The yellow powder was filtered, rinsed with hexanes, and dried under reduced pressure. A 300-mL round-bottom flask equipped with a stir bar, condenser and N$_2$ bubbler was charged with the yellow powder (230 mg) and EtOAc (3 mL). The mixture was heated to reflux, then hexanes (12 mL) was added to the boiling solution. The stir bar was removed, and the flask was capped and allowed cool for 1 h. The powder was filtered, rinsed with hexanes to give an off-white powder (0.17 g, 20%). $^1$H NMR (CD$_2$Cl$_2$, 500 MHz, reference CH$_2$Cl$_2$ δ 5.33) δ 7.35 (s, 3H, pyrimidineC6-H), 7.28 (dt, J=1.3, 7.5 Hz, 3H, ArH), 7.24 (m, 3H, ArH), 7.20 (m, 3H, ArH), 7.13-7.08 (m, 6H, ArH), 6.93 (br, 3H, ArH), 6.86 (m, 15H, ArH), 2.29 (s, 9H, ArCH$_3$), 2.28 (s, 9H, ArCH$_3$), 2.12 (s, 9H, ArCH$_3$), 1.07 (s, 27H, C(CH$_3$)$_3$). $^{13}$C NMR (CD$_2$Cl$_2$, 126 MHz, ref. CH2Cl2 δ 54.24) δ192.4, 174.5, 160.7, 154.5, 145.6, 141.0 (3), 141.0, 139.8, 134.5, 132.8, 131.3, 131.1, 130.8, 126.8, 126.1, 126.0, 125.8, 125.7, 39.7, 30.2, 21.7, 21.6, 20.5.

Synthesis Example 3

This example illustrates the synthesis of Compound L3 and Compound B3.

The synthesis was carried out in five steps as follows:

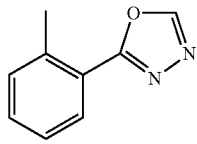

Step 1: Synthesis of 2-(2-Tolyl)[1,3,4]oxadiazole

A 500-mL round-bottom flask equipped with a stir bar, condenser, and $N_2$ bubbler was charged with 2-tolylhydrazide (10 g, 66.58 mmol) and triethyl orthoformate (40 mL). The mixture was stirred and heated under $N_2$ at 160° C. overnight. The mixture was then concentrated under reduced pressure to give an oil. Ethyl acetate was added to the oil and washed with 1N aqueous HCl twice, then washed with brine. The organic layer was separated, dried over $MgSO_4$, filtered, and concentrated under reduced pressure. The crude product was purified by column chromatography (20% ethyl acetate in hexane) to give a colorless oil (7.03 g, 66%) as a product. $^1$H NMR ($CD_2Cl_2$, 499.8 MHz) δ 8.52 (s, 1H), 7.94 (dd, J=1.4, 7.3 Hz, 1H), 7.45 (m, 1H), 7.39-7.33 (m, 2H), 2.70 (s, 3H).

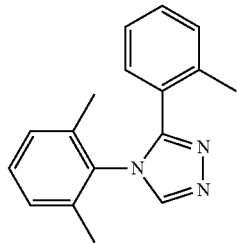 [SMILES: Cc1ccccc1-c1nncn1-c1c(C)cccc1C]

Step 2: Synthesis of 3-(2-Tolyl)-4-(2,6-dimethylphenyl)-4H-[1,2,4]triazole

A 100-mL round-bottom flask equipped with a stir bar, condenser and $N_2$ bubbler was charged with 2-(2-tolyl)[1,3,4]oxadiazole (7.03 g, 43.88 mmol), 2,6-dimethylaniline (5.31 g, 43.88 mmol), and o-dichlorobenzene (24 mL). Trifluoroacetic acid (5 g, 43.88 mmol) was then added. The reaction mixture was stirred at 185° C. for 15 h. Aqueous $Na_2CO_3$ (10%) was added to the reaction mixture until pH ~9 was obtained. The product was extracted twice with $CH_2Cl_2$. The combined organic layers were washed with brine, dried over $MgSO_4$, and concentrated under reduced pressure. By column chromatography (12-70% ethyl acetate in hexane) 7.2 g (62%) of product was obtained as a white solid. $^1$H NMR ($CD_2Cl_2$, 499.8 MHz) δ 8.18 (s, 1H), 7.32-7.29 (m, 1H), 7.27-7.22 (m, 2H), 7.13-7.10 (m, 2H), 6.09 (m, 1H), 6.80 (dd, J=1.3, 7.8 Hz, 1H), 2.51 (s, 3H), 1.98 (s, 6H).

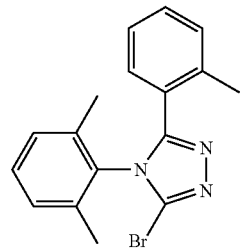 [SMILES: Cc1ccccc1-c1nnc(Br)n1-c1c(C)cccc1C]

Step 3: Synthesis of 3-(2-Tolyl)-5-bromo-4-(2,6-dimethylphenyl)-4H-[1,2,4]triazole A 200-mL round-bottom flask equipped with a stir bar and $N_2$ bubbler was charged with 3-(2-tolyl)-4-(2,6-dimethylphenyl)-4H-[1,2,4]triazole (3.34 g, 12.68 mmol) in THF (100 mL). At −78° C. n-BuLi (7.92 mL, 1.6M, 1 eq.) was added dropwise under nitrogen. The reaction mixture was stirred for 30 min at −78° C., then bromine (2.05 g, 12.68 mmol) was added dropwise. The resultant mixture was stirred for another 30 min at −78° C., then the reaction mixture was warmed up to room temperature. Ethyl acetate and water were added to the mixture, the organic layer was separated, dried over ($MgSO_4$), and concentrated under reduced pressure. By column chromatography (50% ethyl acetate in hexane) 4.1 g of product was obtained as a white solid (94.6% yield). $^1$H NMR ($CD_2Cl_2$, 499.8 MHz) δ 7.32-7.24 (m, 3H), 7.16-7.13 (m, 2H), 7.00-6.96 (m, 1H), 6.81 (dd, J=1.2, 7.7 Hz, 1H), 2.51 (s, 3H), 1.99 (s, 6H).

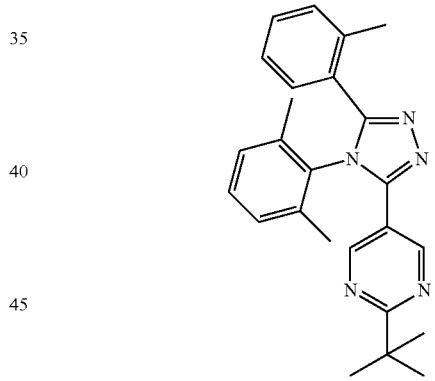

Step 4: Synthesis of 5-[5-(2-Tolyl)-4-(2,6-dimethylphenyl)-4H-[1,2,4]triazol-3-yl]-2-tert-butylpyrimidine, Compound L3

A 2-neck 250-mL round-bottom flask equipped with a stir bar, condenser, $N_2$ bubbler and sparge tube was charged with 2-tert-butyl-5-(4,4,5,5-tetramethyl-[1,2,3]dioxaborolan-2-yl)-pyrimidine (0.95 g, 3.62 mmol), 3-(2-tolyl)-5-bromo-4-(2,6-dimethylphenyl)-4H-[1,2,4]triazole (0.837 g, 2.44 mmol), and $Cs_2CO_3$ (1.59 g, 4.89 mmol). 1,4-Dioxane (35 mL) and water (2 mL) were added. The solution was sparged with $N_2$ for 30 min, then the sparge tube was removed and quickly replaced with a rubber septum. In the glovebox, $Pd_2(dba)_3$ (0.112 g, 0.12 mmol), S-phos (0.201 g, 0.489 mmol) were combined with 1,4-dioxane (5 mL) in a 100-mL round-bottom flask. The flask was sealed with a rubber septum. The mixture was stirred for 20 min, and then removed from dry box. The catalyst solution was transferred to the reaction flask via a cannula. The resultant reaction mixture was stirred for 5 h at 90° C. The mixture was cooled down to room temperature, then transferred to a separatory funnel with EtOAc and water. The organic layer was washed with water and then brine, dried over MgSO$_4$, and concentrated under reduced pressure. By column chromatography (10-30% ethyl acetate in hexane) 0.53 g of product was obtained as a white solid (55% yield). $^1$H NMR (CD$_2$Cl$_2$, 499.8 MHz) δ 8.69 (2, 2H), 7.37-7.32 (m, 2H), 7.30 (dt, J=1.3, 7.5, 1H), 7.19-7.16 (m, 2H), 7.02-6.98 (m, 1H), 6.80 (dd, J=1.3, 7.7, 1 H), 2.57 (s, 3H), 1.95 (s, 6H), 1.38 (s, 9H).

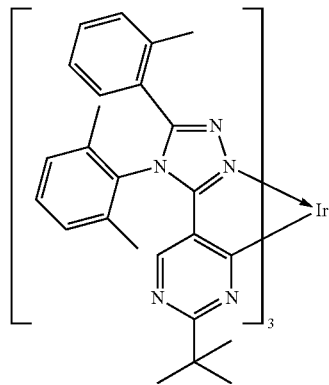

Step 5: Synthesis of Tris{5-[5-(2-toly)-4-(2,6-dimethylphenyl)-4H-1,2,4-triazol-3-yl-kN$^2$]-2-tert-butylpyrimidin-4-yl-kC$^4$}iridium, Compound B3

A 20-mL vial was charged with iridium acetylacetonate (0.194 g, 0.39 mmol) and 5-[5-(2-tolyl)-4-(2,6-dimethylphenyl)-4H-[1,2,4]triazol-3-yl]-2-tert-butylpyrimidine (0.52 g, 1.31 mmol). The content was mixed and transferred a 7-mL pressure tube and sealed under N$_2$. The tube was heated 250° C. for 48 h. The reaction mixture was purified by column chromatography (15-100% ethyl acetate in hexane) to provide 400 mg (73% yield) of mixture of mer-/fac-isomer (46:54) as a solid. This mixture was tried for isomerization to fac-isomer by reflux in ethylene glycol (20-mL) at 200° C. for 48 h under nitrogen. The precipitated solid material at room temperature was collected and further purified by column chromatography (15-60% ethyl acetate in hexane) to give a white solid as a fac-isomer (0.1 g, 25% yield). $^1$H NMR (CD$_2$Cl$_2$, 499.8 MHz) δ7.33 (t, J=7.63, 1H), 7.28-7.19 (m, 3H), 7.16 (d, J=7.6, 1H), 7.10 (s, 1H), 6.97-6.93 (m, 1H), 6.90-6.87 (m, 1H), 2.40 (s, 3H), 2.12 (s, 3H), 1.83 (s, 3H), 0.99 (s, 9H). $^{13}$C NMR (CD$_2$Cl$_2$, 126 MHz) δ174.4, 159.1, 152.7, 144.2, 139.3, 136.3, 132.9, 131.6, 130.6, 130.0, 129.6, 129.5, 128.9, 125.7, 125.5, 125.4, 39.2, 29.7, 20.8, 18.1, 18.0.

Synthesis of Comparative Compounds A, B, and C

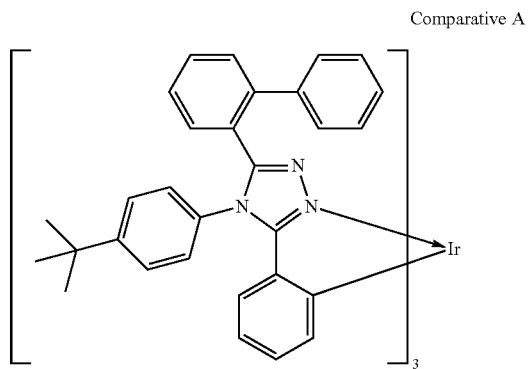

Comparative A

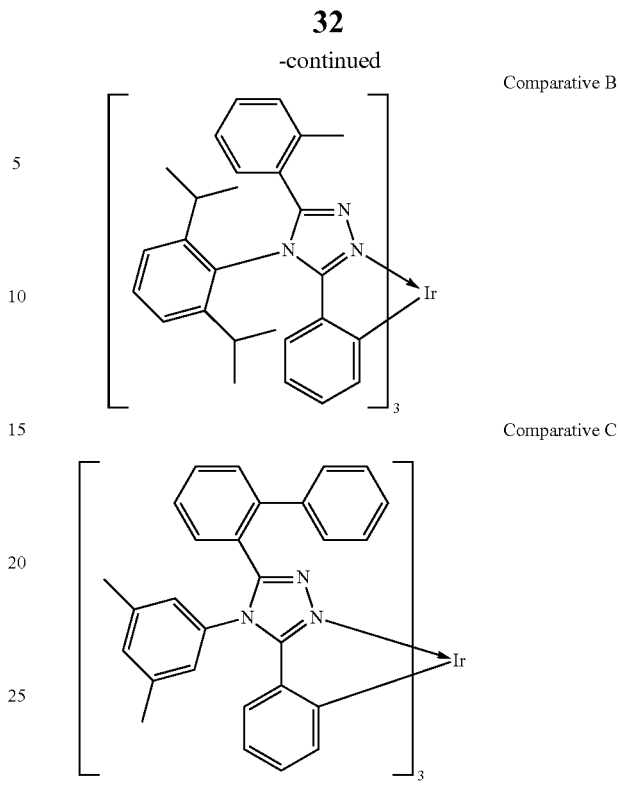

Comparative Compound A was synthesized in 3 steps similar to those for Comparative Compound C as follows.

Step 1: Synthesis of 2-(biphenyl-2-yl)-5-phenyl-1,3,4-oxadiazole

To a solution of biphenylcarboxylic acid (5.00 g, 25.2 mmol) in (CH$_2$Cl$_2$, 50 mL) at −5° C., was added a catalytic amount of anhydrous DMF (3 drops). This was followed by the dropwise addition of oxalyl chloride (3.2 mL, 38 mmol) in CH$_2$Cl$_2$ (12.5 mL). The reaction was allowed to warm to ambient temperature and stirred for 16 h. The reaction mixture was concentrated under reduced pressure to about ~5.8 g of acid chloride, which was used immediately without further characterization. In the fume hood, 5-phenyl-1H-tetrazole (3.4 g, 23 mmol) was added to an oven dried 250 mL 2-neck RBF containing a magnetic stir bar, followed by careful dropwise addition of the acid chloride and then pyridine (30 mL). The reaction mixture was stirred at 90° C. until GC/MS analysis showed full conversion of the starting materials. The reaction mixture was transferred to a 1-neck tear-drop flask with the aid of toluene (30 mL). The mixture was concentrated under reduced pressure. Biotage® purification was performed to yield a colorless solid (5 g, 70%). $^1$H NMR (500 MHz, CD$_2$Cl$_2$, reference peak: CH$_2$Cl$_2$ δ 5.30) δ 8.13 (m, 1H, ArH), 7.63-7.59 (m, 3H, ArH), 7.53 (dt, J=1.4, 7.6 Hz, 1H, ArH), 7.49-7.45 (m, 2H, ArH), 7.41-7.37 (m, 5H, ArH), 7.33-7.29 (m, 2H, ArH).

Step 2: Synthesis of 3-(biphenyl-2-yl)-4-(3,5-dimethylphenyl)-5-phenyl-4H-1,2,4-triazole Inside the glove box, 3,5-dimethylaniline (1.14 g, 9.41 mmol) was added to a 25-mL Schlenck tube containing a stir bar. The reaction mixture was stirred and treated with anhydrous aluminum chloride (0.35 g, 2.6 mmol) in small portions to give a light tan solid. The mixture was stirred at 140° C. for 70 min. Next, the mixture was treated with 2-(biphenyl-2-yl)-5-phenyl-1,3,4-oxadiazole (1.04 g, 3.49 mmol) followed by anhydrous NMP (1.0 mL) and then stirred at 210° C. for 16 h, after which the mixture solidified. Water (10 mL) and ethyl acetate (10 mL) were added along with a stir bar to break up the solid. The crude product was extracted with ethyl acetate (50 mL) and washed with brine. The product was purified by Biotage® chromatography to give a semi crystalline white solid (1.02 g, 73%). $^1$H NMR (500 MHz, CD$_2$Cl$_2$, reference peak: CH$_2$Cl$_2$ δ 5.30) δ 7.70 (dd, J=1.4, 7.5 Hz, 1H, ArH), 7.48 (m, 2H, ArH), 7.31-7.27 (m, 4H, ArH), 7.23-7.12 (m, 5H, ArH), 6.87-6.84 (m, 2H, ArH), 6.79 (s, 1H, ArH), 5.78 (s, 2H, ArH), 1.97 (s, 6H, ArH). Purity (LC-MS, UV/Vis) 99.67%

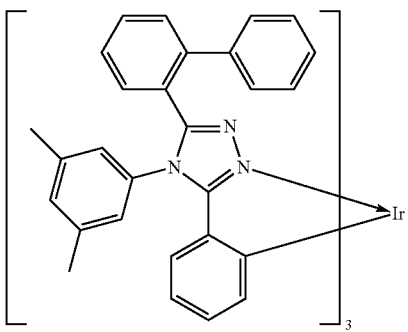

Step 3: Synthesis of tris{2-[5-(biphenyl-2-yl)-4-(3,5-dimethylphenyl)-4H-1,2,4-triazol-3-yl-κN$^2$]phenyl-κC$^1$}iridium A 20-mL scintillation vial was charged with 3-(biphenyl-2-yl)-4-(3,5-dimethylphenyl)-5-phenyl-4H-1,2,4-triazole (1.00 g, 2.49 mmol) and iridium acetylacetonate (0.37 g, 0.76 mmol) and the mixture was transferred to a stainless steel pressure tube. The tube was sealed under N$_2$ and heated at 250° C. for 36 h. The product was rinsed from the pressure tube with CH$_2$Cl$_2$ and concentrated under reduced pressure. The solid (0.20 g) was recrystallized in refluxing acetone under nitrogen and allowed to cool to room temperature slowly to give a yellow powder (0.11 g, 10%). $^1$H NMR (500 MHz, CD$_2$Cl$_2$, reference peak: CH$_2$Cl$_2$ δ 5.30) δ 7.86 (b, 3H, ArH), 7.52-7.40 (b, 6H, ArH), 7.32 (b, 3H, ArH), 7.19 (b, 3H, ArH), 7.00-6.70 (b, 21H, ArH), 6.55 (b, 4H, ArH), 6.35 (b, 4H, ArH), 5.8 (b, 4H, ArH), 2.14-1.93 (b, 6H, CH$_3$). LC-MS (SQ with ESI) C$_{84}$H$_{66}$IrN$_9$ calcd: 1394.78 ([M+H]+). Found: 1395.60. Purity (LC-MS, UV/Vis)>99.32%.

Comparative Compound B was synthesized in five steps as follows:

Step 1: Synthesis of 2-phenyl-1,3,4-oxadiazole

Benzhydrazide (21.66 g, 159.0 mmol) and triethyl orthoformate (90 mL) were placed in a 500-mL, two-neck round-bottom flask, and the mixture was vigorously stirred at 160° C. for 24 h. After cooling to room temperature, the solvent was evaporated under reduced pressure. The product was used for the next step without further purification. $^1$H NMR (500 MHz, CD$_2$Cl$_2$) δ 8.47 (s, 1H, oxadiazoleC5-H), 8.07-8.05 (m, 2H, ArH), 7.58-7.50 (m, 3H, ArH).

Step 2: 4-(2,6-Diisopropylphenyl)-3-phenyl-4H-[1,2,4]triazole

3-Phenyl-1,3,4-oxadiazle (9.0 g, 62 mmol), 2,6-diisopropylaniline (11.6 mL, 61.5 mmol), and o-dichlorobenzene (30 mL) were combined into a 100-mL round-bottom flask equipped with a stir bar, condenser and N$_2$ bubbler. Trifluoroacetic acid (4.7 mL, 61.4 mmol) was added. The flask was placed in an aluminum block set at 182° C. The reaction mixture was refluxed for 16 h. After cooling to room temperature, it was poured into 10% aqueous sodium carbonate (200 mL). The mixture was adjusted to pH ~10 and then transferred to a separatory funnel. The product was extracted with dichloromethane two times. The organic layers were combined and washed with brine, dried over MgSO$_4$, filtered, and concentrated under reduced pressure. o-Dichlorobenzene was vacuum distilled at 90° C. to give a pink solid. The crude product was purified by automated column chromatography on a 340-g KP-Sil® cartridge with a liquid load from CH$_2$Cl$_2$ to give an oil (11 g, 58%). $^1$H NMR (500 MHz, CD$_2$Cl$_2$) δ 8.11 (s, 1H, triazoleC5-H), 7.50 (t, J=7.8 Hz, 1H, ArH), 7.46-7.44 (m, 2H, ArH), 7.35-7.24 (m, 5H, ArH), 2.37 (sept, J=6.8 Hz, 2H, CH(CH$_3$)$_2$), 1.09 (d, J=6.8 Hz, 6H, CH(CH$_3$)$_2$), 0.89 (d, J=6.8 Hz, 2H, CH(CH$_3$)$_2$).

Step 3: Synthesis of 3-bromo-4-(2,6-diisopropylphenyl)-5-phenyl-4H-[1,2,4]triazole A 1-L round-bottom flask equipped with a stir bar, condenser and N$_2$ bubbler was charged with 4-(2,6-diisopropylphenyl)-3-phenyl-4H-[1,2,4]triazole (9.9 g, 32 mmol), N-bromosuccinimide (7.2 g, 40. mmol), carbon tetrachloride (60 mL), and acetic acid (60 mL). The flask was placed in an aluminum block set at 120° C. The reaction was monitored by TLC (3:2 CH$_2$Cl$_2$:EtOAc) after 4 h to show a product forming. After 4.5 h, more N-bromosuccinimide (1.5 g) was added to the reaction. After 6.5 h, TLC showed a faint spot corresponding to the starting triazole. The flask was lifted out of the aluminum block after 7.75 h. Aqueous Na$_2$CO$_3$ (10%) was added to the reaction mixture until the pH was ~8. The product was extracted with CH$_2$Cl$_2$ three times. And the combined organic layers were washed with brine, dried over MgSO$_4$, filtered, concentrated under reduced pressure to give an oil (15.2 g). The product was purified on Biotage® flash column chromatography on a 340 g KP-Sil® cartridge with a liquid load from CH$_2$Cl$_2$ to give a white powder (10 g, 80%). $^1$H NMR (500 MHz, CD$_2$Cl$_2$) δ 7.57 (t, J=7.8 Hz, 1H, ArH), 7.46 (m, 2H, ArH), 7.36-7.32 (m, 3H, ArH), 7.25 (m, 2H, ArH), 2.32 (sept, J=6.8 Hz, 2H, CH(CH$_3$)$_2$), 1.66 (d, J=6.8 Hz, 6H, CH(CH$_3$)$_2$), 0.86 (d, J=6.8 Hz, 6H, CH(CH$_3$)$_2$.

Step 4: Synthesis of 3-(o-tolyl)-4-(2,6-diisopropylphenyl)-5-phenyl-4H-[1,2,4]triazole A 1-L, 2-neck round-bottom flask equipped with a stir bar, reflux condenser, N$_2$ bubbler, and a N$_2$ sparge tube was charged with 3-bromo-4-(2,6-diisopropyl-phenyl)-5-phenyl-4H-[1,2,4]triazole (9.0 g, 23 mmol), o-tolylboronic acid (6.36 g, 46.8 mmol), nitrogen-sparged toluene (360 mL), and K$_3$PO$_4$ monohydrate (16.2 g, 70.3 mmol). The mixture was sparged with N$_2$ for 30 min. The sparge tube was replaced with a rubber septum. In the glovebox, Pd$_2$dba$_3$ (0.43 g, 0.47 mmol), S-Phos (0.77 g, 1.9 mmol), and toluene (100 mL) were combined in a sealed round-bottom flask and stirred at room temperature for 20 minutes. The flask was removed from the glovebox. The catalyst solution was transferred to the reaction vessel via a cannula. The reaction mixture was stirred with the aluminum block set at 140° C. for 150 min. TLC (1:1 EtOAc:hexanes) showed full conversion of bromotriazole. After the reaction mixture was cooled, it was diluted with dichloromethane and passed through a plug of silica gel topped with Celite® and then rinsed with 1:1 EtOAc:CH$_2$Cl$_2$, and concentrated under reduced pressure to give an orange solid (11.4 g). The crude product was purified by Biotage® flash column chromatography on a 340 g KP-Sil® cartridge with a liquid load from minimal dichloromethane to give a colorless powder (8.95 g, 97%). The powder was suspended in hexanes (250 mL) and heated to reflux. The sample had poor solubility, thus EtOAc was added slowly until the solid was dissolved. The solution was clear after addition of EtOAc (50 mL). Hexanes (75 mL) were added slowly. The solution remained clear. The flask was capped and allowed to cool to room temperature. Crystals began to form on the wall of the flask. The flask was stored in a refrigerator for 2 h. The crystals were isolated by decanting the mother liquor and the crystals were washed with hexanes. The crystals were placed under reduced pressure (~100 mTorr) to give a white powder (6.2 g, 67%). $^1$H NMR (500 MHz, CD$_2$Cl$_2$) δ7.45-7.40 (m, 3H, ArH), 7.34-7.31 (m, 2H, ArH), 7.27-7.24 (m, 2H, ArH), 7.22-7.17 (m, 3H, ArH), 6.90 (t, J=7.5 Hz, 1H, ArH), 6.75 (d, J=7.5 Hz, 1H, ArH), 2.57 (s, 3H, ArCH$_3$), 2.41 (sept, J=6.8 Hz, 2H, CH(CH$_3$)$_2$), 0.80 (d, J=6.8 Hz, 6H, CH(CH$_3$)$_2$, 0.72 (d, J=6.7 Hz, 6H, CH(CH$_3$)$_2$.

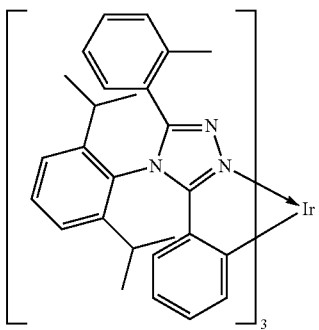

Step 5: Synthesis of tris(2-{4-[2,6-di(propan-2-yl) phenyl]-5-(2-methylphenyl)-4H-1,2,4-triazol-3-yl-kN$^2$}phenyl-kC$^1$)iridium 3-(o-Tolyl)-4-(2,6-diisopropylphenyl)-5-phenyl-4H-[1,2,4]triazole (6.0 g, 15 mmol) and Ir(acac)$_3$ (2.25 g, 4.60 mmol) were combined, mixed in a 40-mL glass bottle and heated in a 75-mL shaker tube at 250° C. for 72 h. The crude solid was scraped and rinsed from tube with CH$_2$Cl$_2$. The resulting mixture was concentrated under reduced pressure to give a beige solid (7.4 g). The next day, dichloromethane (200 mL) was added to the solid and the resulting mixture was heated to boiling, and then allowed to cool. The insoluble material (400 mg) was removed by vacuum filtration. The filtrate was loaded on a plug of silica gel (180 g) and then rinsed with 5%, 10%, 15%, and then 20% EtOAc/hexanes to isolate the product. The fractions containing the product were concentrated. The insoluble material (400 mg) was dissolved in 50-mL boiling dichloromethane and allowed to cool. The solution was loaded on a plug of silica gel (50 g) and then eluted with EtOAc/hexanes. The fractions containing the product were isolated and combined with product fractions from the previous elution. The combined solution was concentrated under reduced pressure to give a yellow solid (2.15 g). The 180-g plug of silica gel was flushed with 5% EtOAc/CH$_2$Cl$_2$ (1 L) and the resulting solution was concentrated under reduced pressure to give a solid (3.85 g). The 2.15 g and 3.85 g samples were combined in dichloromethane and the solution was concentrated under reduced pressure to give 5.9 g of a solid. The sample was dissolved in boiling toluene (150 mL), then EtOAc (300 mL) was added slowly via addition funnel. The flask was then capped and allow to cool to room temperature. Precipitates began to form upon cooling. After 2 days, the solid was filtered and rinsed with EtOAc. It was placed under vacuum (~100 mTorr) to give a bright yellow powder (5.3 g, 78%). $^1$H NMR (500 MHz, CD$_2$Cl$_2$) δ 7.47 (t, J=7.8 Hz, 3H, ArH), 7.23 (d, J=7.8 Hz, 6H, ArH), 7.20 (m, 3H, ArH), 7.15 (m, 3H, ArH), 6.86 (t, J=7.3 Hz, 3H, ArH), 6.82-6.80 (m, 6H, ArH), 6.66 (dt, J=1.0, 7.4 Hz, 3H, ArH), 6.48 (m, 3H, ArH), 6.16 (d, J=7.8 Hz, 3H, ArH), 2.79 (sept, J=6.8 Hz, 3H, CH(CH$_3$)$_2$), 2.28 (s, 9H, ArCH$_3$), 2.25 (sept, J=6.8 Hz, 3H, CH(CH$_3$)$_2$), 0.92 (d, J=6.7 Hz, 9H, CH(CH$_3$)$_2$), 0.79 (d, J=6.7 Hz, 9H, CH(CH$_3$)$_2$), 0.74 (d, J=6.8 Hz, 9H, CH(CH$_3$)$_2$), 0.70 (d, J=6.8 Hz, 9H, CH(CH$_3$)$_2$). LC/MS (SQ with ESI) C$_{81}$H$_{84}$IrN$_9$ calcd: 1376.89 ([M+H]+). Found: 1376.31. Purity (LC-MS, UV-Vis): >99.9%.

Photophysical properties of the synthesized emitters were characterized by UV-Vis absorption, luminescence, photoluminescent quantum efficiency (PLQE) and photoluminescent lifetime. Solutions of the compounds were prepared in spectroscopic grade toluene at concentrations of ~10 μm. The solutions were degassed by four rounds of freeze-pump-thaw. The absorption spectra were recorded using an Ocean Optics Chem2000-UV-Vis unit. The luminescence spectra were measured with a Fluorolog (ISA Jobin-Yvon-Spex) with excitations at 300, 320, 340, and 360 nm. Emission spectra were independent of excitation wavelength. The photoluminescent quantum yield (PLQE) was measured relative to a freshly prepared solution of quinine sulfate, for which the PLQE was assumed to be 0.57 (57%). The lifetime of the triplet state was measured using a Horiba TemPro 01 time-correlated, single photon counting (TC-SPC) unit, with excitation set at 343 nm. The phosphorescent lifetime was measured at the highest energy peak in the emission spectrum.

Device Examples

These examples demonstrate the fabrication and performance of OLED devices.

(1) Materials

HIJ-1 is an electrically conductive polymer doped with a polymeric fluorinated sulfonic acid. Such materials have been described in, for example, published U.S. patent applications US 2004/0102577, US 2004/0127637, US 2005/0205860, and published PCT application WO 2009/018009.

HT-1 is a triarylamine-containing polymer. Such materials have been described in, for example, published PCT application WO 2009/067419.

Host-1 is the carbazole-furan derivative shown below

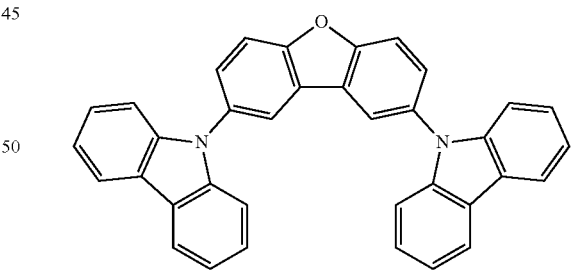

ET-1 is a metal quinolate complex.

Comparative Compounds A, B, and C are discussed above. The devices had the following structure on a glass substrate:

anode=Indium Tin Oxide (ITO), 50 nm
hole injection layer=HIJ-1 (50 nm)
hole transport layer=HT-1 (20 nm)
photoactive layer, discussed below=100:14 Host:dopant ratio (43 nm);
anti-quenching layer=Host-1 (10 nm)
electron transport layer=ET-1 (10 nm)
electron injection layer/cathode=CsF/Al (1/100 nm)

(2) Device Fabrication

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication; the cleaned, patterned ITO substrates were treated with UV ozone for 10 minutes. Immediately after cooling, an aqueous dispersion of HIJ-1 was spin-coated over the ITO surface and heated to remove solvent. After cooling, the substrates were then spin-coated with a hole transport solution, and then heated to remove solvent. The substrates were masked and placed in a vacuum chamber. The photoactive layer, the electron transport layer and the anti-quenching layer were deposited by thermal evaporation, followed by a layer of CsF. Masks were then changed in vacuo and a layer of Al was deposited by thermal evaporation. The chamber was vented, and the devices were encapsulated using a glass lid, desiccant, and UV curable epoxy.

(3) Materials and Device Characterization

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence luminance of the LED by the current density needed to run the device. The unit is a cd/A. The color coordinates were determined using either a Minolta CS-100 meter or a Photoresearch PR-705 meter.

Examples 1, 2 and 3, and Comparative Examples A, B, and C

TABLE I

Photoluminescent (PL) properties of blue emitters in toluene

| Example | Emitter | PL Peaks (nm) | PL Quantum Yield (%) |
|---|---|---|---|
| 1 | B1 | 448, 477 | 72.3 |
| 2 | B2 | ~450, 481 | 71.3 |
| 3 | B3 | ~450, 481 | 82.5 |
| A | Comparative A | 475, 502 | 98 |
| B | Comparative B | 476, 502 | 88.6 |
| C | Comparative C | 476, 501 | 96 |

As can be seen from Table I, the compounds having the structure of Formula II all show deeper blue luminance than the comparative compounds. The photoluminance quantum yields also indicate the compounds having the structure of Formula II are efficient photoluminescent emitters.

Examples 4, 5 and 6, and Comparative Examples D, E, and F

TABLE II

Device results

| Example | Dopant | Host | EL Peak (nm) | CIE (x, y) |
|---|---|---|---|---|
| 4 | B1 | Host-1 | 472 | (0.164, 0.215) |
| 5 | B2 | Host-1 | 441 | (0.162, 0.113) |
| 6 | B3 | Host-1 | 441 | (0.163, 0.128) |
| D | Comparative A | Host-1 | 478 | (0.192, 0.406) |
| E | Comparative B | Host-1 | 476 | (0.183, 0.372) |
| F | Comparative C | Host-1 | 477 | (0.181, 0.371) |

All data @ 1000 nits. CIE(x,y) are the x and y color coordinates according to the C.I.E. chromaticity scale (Commission Internationale de L'Eclairage, 1931.

Devices made for the generation of data in Table II were built to demonstrate the color characteristics of the compounds of Formula II and not necessarily optimized for other operational parameters. It can be seen from the results in Table II that the peak wavelength is blue-shifted and the CIE(xy) color is deeper blue in the devices including dopants of Formula II.

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A compound having Formula II

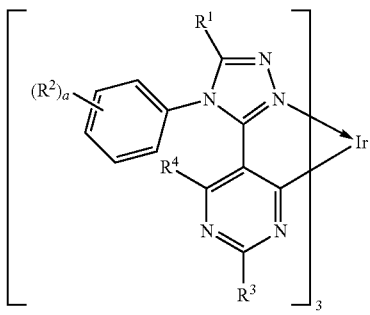

Formula II wherein:
- $R^1$ is an aryl group or deuterated aryl group having 6-20 carbons;
- $R^3$ is selected from the group consisting of alkyl, branched alkyl, cyclic alkyl, silyl, aryl, deuterated alkyl, deuterated branched alkyl, deuterated cyclic alkyl, deuterated silyl, and deuterated aryl;
- $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
- $R^4$ is H or D; and
- a is an integer from 0-5.

2. The compound of claim 1, wherein the compound is at least 10% deuterated.

3. The compound of claim 1, wherein $R^1$ and $R^3$ are the same.

4. The compound of claim 1, wherein $R^1$ and $R^3$ are different.

5. The compound of claim 1, wherein $R^1$ is further substituted at any available position with a group selected from alkyl, branched alkyl, aryl, and deuterated analogs thereof.

6. The compound of claim 5, wherein $R^3$ is a branched alkyl group or deuterated branched alkyl group having 4-6 carbons.

7. The compound of claim 6, wherein a>0.

8. The compound of claim 7, wherein $R^2$ is an alkyl or deuterated alkyl group having 1-6 carbons.

9. The compound of claim 7, wherein $R^2$ is a branched alkyl or deuterated branched alkyl group having 4-6 carbons.

10. The compound of claim 1 selected from B1 through B3.

Compound B1

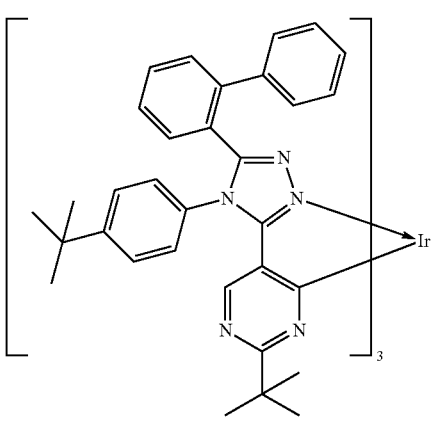

Compound B2

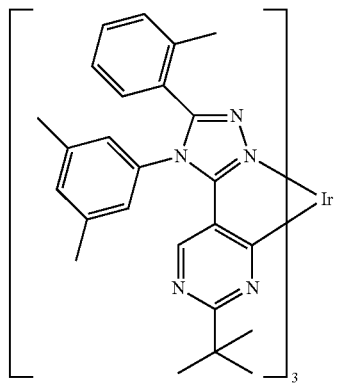

Compound B3

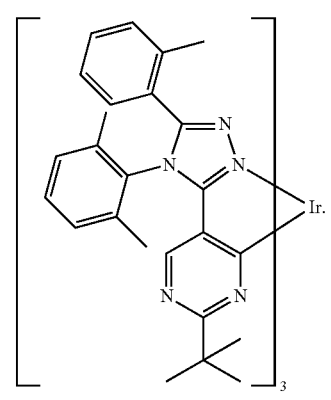

11. An organic electronic device comprising a first electrical contact, a second electrical contact and a photoactive layer therebetween, the photoactive layer comprising a compound having Formula II Formula II

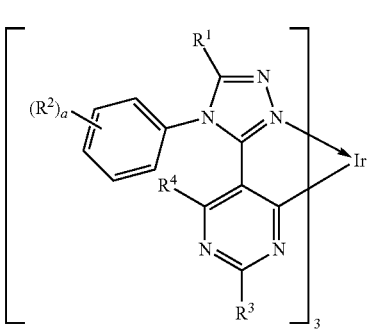

wherein:
- $R^1$ is an aryl group or deuterated aryl group having 6-20 carbons;
- $R^3$ is selected from the group consisting of alkyl, branched alkyl, cyclic alkyl, silyl, aryl, deuterated alkyl, deuterated branched alkyl, deuterated cyclic alkyl, deuterated silyl, and deuterated aryl;
- $R^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
- $R^4$ is H or D; and
- a is an integer from 0-5.

12. The device of claim 11, wherein the photoactive layer further comprises a host material.

13. The device of claim 11, wherein the photoactive layer consists essentially of the compound of Formula II and a host material.

14. A compound having Formula I

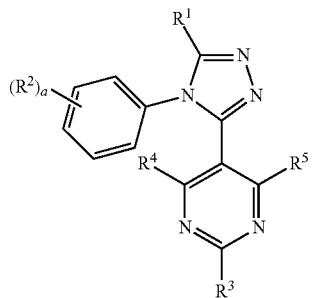

Formula I wherein:
R$^1$ is an aryl group or deuterated aryl group having 6-20 carbons;
R$^3$ is selected from the group consisting of alkyl, branched alkyl, cyclic alkyl, silyl, aryl, deuterated alkyl, deuterated branched alkyl, deuterated cyclic alkyl, deuterated silyl, and deuterated aryl;
R$^2$ is the same or different at each occurrence and is selected from the group consisting of D, alkyl, branched alkyl, cyclic alkyl, silyl, aryl, deuterated alkyl, deuterated branched alkyl, deuterated cyclic alkyl, deuterated silyl, and deuterated aryl;
R$^4$- R$^5$ are the same or different at each occurrence and are H or D; and
a is an integer from 0-5.

15. The compound of claim 14, wherein R$^1$ and R$^3$ are different groups.

16. The compound of claim 15, wherein R$^3$ is a branched alkyl group or deuterated branched alkyl group having 4-6 carbons.

17. The compound of claim 16, wherein a>0 and R$^2$ is an alkyl or deuterated alkyl group having 1-6 carbons.

18. The compound of claim 16, wherein a>0 and R$^2$ is a branched alkyl or deuterated branched alkyl group having 4-6 carbons.

* * * * *